United States Patent
Hayashi

(10) Patent No.: US 10,663,444 B2
(45) Date of Patent: May 26, 2020

(54) METHOD FOR EVALUATING EXHAUST GAS SIMULATION

(71) Applicant: DENSO CORPORATION, Kariya, Aichi-pref. (JP)

(72) Inventor: Naohiro Hayashi, Kariya (JP)

(73) Assignee: DENSO CORPORATION, Kariya (JP)

(*) Notice: Subject to any disclaimer, the term of this patent is extended or adjusted under 35 U.S.C. 154(b) by 260 days.

(21) Appl. No.: 15/901,011

(22) Filed: Feb. 21, 2018

(65) Prior Publication Data

US 2018/0238847 A1    Aug. 23, 2018

(30) Foreign Application Priority Data

Feb. 22, 2017    (JP) ................... 2017-031185

(51) Int. Cl.
*G06F 11/30*    (2006.01)
*G01N 33/00*    (2006.01)
(Continued)

(52) U.S. Cl.
CPC ........... *G01N 33/0067* (2013.01); *F01N 3/10* (2013.01); *F01N 11/00* (2013.01);
(Continued)

(58) Field of Classification Search
CPC ................................. G01N 33/0067
See application file for complete search history.

(56) References Cited

U.S. PATENT DOCUMENTS

| | | | |
|---|---|---|---|
| 6,438,946 B1 * | 8/2002 | Majima | F02D 41/1441 60/276 |
| 2005/0268597 A1 * | 12/2005 | Kosaka | F01N 3/023 60/277 |
| 2011/0106397 A1 | 5/2011 | Muta et al. | |

FOREIGN PATENT DOCUMENTS

| | | |
|---|---|---|
| JP | 9-304421 | 11/1997 |
| JP | 2003-130703 | 5/2003 |

(Continued)

OTHER PUBLICATIONS

Salasc, Sophie et al., "Impact of Manifold Design on Flow Distribution of a Close-Coupled Catalytic Converter", SAE Technical Paper Series, 2005 SAE World Congress, Detroit, Michigan, Apr. 11-14, 2005 (16 pgs.).

Hasegawa, Hirokazu et al., "Engine Technology for skyactiv-g on CX-5", Mazda technical report No. 30(2012), 2012 (6 pgs.) and translation (1 pg.).

Kojima, Tadatomo et al., "Research and Development on Flow in High Effective Converter for Automobile by CFD", Kinki University next generation infrastructure technology Institute report, vol. 2 (2011) 101-106, 2011 (6 pgs.) and translation (10 pgs.).

(Continued)

*Primary Examiner* — Phuong Huynh
(74) *Attorney, Agent, or Firm* — Nixon & Vanderhye P.C.

(57) ABSTRACT

Evaluation method of exhaust gas simulation capable of simply and appropriately evaluating the validity of the simulation is provided. In analysis data, an analysis amplitude curve is calculated in which a change in the concentration of virtual exhaust gas at the observation point in the converged pipe portion is plotted, and an analysis time interval between the zero point and the reference point in the analysis amplitude curve is plotted. In actual measurement data, an actual amplitude curve is provided in which a change in the specific gas component at an observation point is measured with time, and an actual time interval is provided in which a time interval from a zero point to a reference point in the actual amplitude curve. The analysis data is determined as valid when a difference between the analysis time interval and the actual time interval is within a predetermined correlation range.

7 Claims, 14 Drawing Sheets

(51) Int. Cl.
*F01N 3/10* (2006.01)
*F01N 11/00* (2006.01)
*G06F 30/15* (2020.01)
*G06F 30/23* (2020.01)
*G01M 15/10* (2006.01)
*G06F 111/10* (2020.01)

(52) U.S. Cl.
CPC ......... *G01N 33/0073* (2013.01); *G06F 30/15* (2020.01); *G06F 30/23* (2020.01); *F01N 2900/0406* (2013.01); *F01N 2900/1402* (2013.01); *G01M 15/102* (2013.01); *G01N 2033/0068* (2013.01); *G06F 2111/10* (2020.01); *Y02T 10/47* (2013.01)

(56) References Cited

FOREIGN PATENT DOCUMENTS

| JP | 2005/49204 | 2/2005 |
| JP | 2005-127818 | 5/2005 |

OTHER PUBLICATIONS

Iwata, Yoshibumi, "Performance Development with a Single-cylinder Engine—Combustion System Improvement for Optimizing Engine Performance", Technical paper, Yamaha Motor Technical Review, Jul. 25, 2005 (10 pgs.) and translation (8 pgs.).

\* cited by examiner

METHOD FOR EVALUATING EXHAUST GAS SIMULATION

CROSS-REFERENCE TO RELATED APPLICATION

This application is based on and claims the benefit of priority from earlier Japanese Patent Application No. 2017-31185 filed Feb. 22, 2017, the description of which is incorporated herein by reference.

BACKGROUND

Technical Field

The present disclosure relates to a method for evaluating an exhaust gas simulation in which validity of analysis data is evaluated by comparing analysis data and actual measurement data.

Description of the Related Art

In an exhaust pipe of the internal combustion engine, a catalytic converter is provided to convert a toxic substance to be relatively harmless substance. An exhaust manifold is disposed between the cylinders and the catalytic converter, and exhaust gasses exhausted from the cylinders are lead to the catalytic converter through the exhaust manifold. To effectively function the catalytic converter, it is preferable to uniformize flow velocity distribution and concentration distribution of the exhaust gas as much as possible. As a technique for predicting the flow velocity distribution and the concentration distribution, a simulation using computational fluid dynamics (CFD) is known. However, since the validity of this simulation is unknown, exhaust gas flow is actually measured with actual equipment to verify the simulation result.

As equipment performing actual measurement of exhaust gas flow, for example, Japanese Patent Application Laid-Open Publication Number 2009-168688 discloses a fluid measurement apparatus. This patent literature discloses a configuration in which a pair of detecting portions are provided separately in an upstream side and a downstream side of a pipe through which fluid flows, and the velocity of the fluid is calculated based on a time difference between state changes of the fluid detected by the pair of detecting portions.

In this regard, a specific method has not been established for evaluating simulation result using the CFD analysis. The above-mentioned patent literature merely discloses a measurement of fluid velocity in the actual equipment and does not disclose or mention a relationship between the actual measurement and the simulation result. When assuming that the fluid velocity actually measured in the actual equipment and the fluid velocity of the simulation result are compared, a large number of measurement points is required for comparing the fluid velocity between the actual measurement and the simulation. Hence, work load increases for measuring the fluid velocity in actual equipment.

SUMMARY

The present disclosure has been achieved in light of the above-mentioned circumstances and provides a method for evaluating an exhaust gas simulation, capable of simply and appropriately evaluating the validity of analysis data of the simulation.

A first aspect of the present disclosure is a method for evaluating an exhaust gas simulation, in which a computer simulation based on a fluid dynamics analysis and an actual measurement are applied to an exhaust gas flow which is a flow of an exhaust gas in an exhaust pipe of an internal combustion engine so as to obtain an analysis data and a measurement data respectively, the exhaust pipe having a converged pipe portion in which a plurality of input pipe portions are converged and a catalyst is disposed, the input pipe portions being respectively connected to a plurality of cylinders of the internal combustion engine; the computer simulation and the actual measurement are applied to the exhaust gas in the converged pipe portion, and the analysis data and the measurement data are compared, thereby evaluating a validity of the analysis data.

The method including steps of: setting, in the analysis data, various conditions including a three-dimensional shaped model of the exhaust pipe, a physical property of a virtual exhaust gas, an inflow time interval of the virtual exhaust gas between the plurality of cylinders in which the virtual exhaust gas successively flows into the input pipe portions at a constant time interval, an inflow boundary condition of the virtual exhaust gas at an input of the input pipes, and an outflow boundary condition of the virtual exhaust gas at an output of the converged pipe portion; determining any of cylinders in the plurality of cylinders to be a specific cylinder and the input pipe portion connected to the specific cylinder to be a specific input portion; dividing the area of the exhaust pipe into a plurality of finite elements; setting, when calculating transfer of the virtual exhaust gas between the finite elements, identification information to identify a virtual exhaust gas flowing into the finite elements of the specific input pipe portion from the specific cylinder, and a virtual exhaust gas flowing into the finite elements of the rest of input pipe portions excluding the specific input pipe portion from the rest of the cylinders excluding the specific cylinder; calculating an analysis amplitude curve representing a change in concentration of the virtual exhaust gas with time at an observation finite element in the observation point of the converged pipe portion, the virtual exhaust gas being exhausted from the specific cylinder to the exhaust pipe, and an analysis time interval representing a time interval from a zero point relative to the time course during the computer simulation to the reference point in the analysis amplitude curve; setting, in the measurement data, an air-fuel ratio of the rest of the cylinders excluding the specific cylinder to be within a predetermined range and an air-fuel ratio of the specific cylinder to be beyond the predetermined range; measuring, for the exhaust gas exhausted to the exhaust pipe from the specific cylinder during a combustion operation of the internal combustion engine, a change in the specific gas component with time at the observation point of the converged pipe portion, thereby obtaining an actual amplitude curve; calculating a time interval from a zero point in the measuring to a reference point in the actual amplitude curve to obtain an actual time interval; and determining that the analysis data is valid, when a difference between the analysis time interval and the actual time interval is within a predetermined correlation range.

Another aspect of the present disclosure is a method for evaluating an exhaust gas simulation, in which a computer simulation based on a fluid dynamics analysis and an actual measurement are applied to an exhaust gas flow which is a flow of an exhaust gas in an exhaust pipe of an internal combustion engine so as to obtain analysis data and measurement data respectively, the exhaust pipe having a converged pipe portion in which a plurality of input pipe portions are converged and a catalyst is disposed, the input pipe portions being respectively connected to a plurality of cylinders of the internal combustion engine; the computer simulation and the actual measurement are applied to the exhaust gas in the converged pipe portion, and the analysis data and the measurement data are compared, thereby evaluating a validity of the analysis data.

The method including steps of: setting, in the analysis data, various conditions including a three-dimensional shaped model of the exhaust pipe, a physical property of a virtual exhaust gas, an inflow time interval of the virtual exhaust gas between the plurality of cylinders in which the virtual exhaust gas successively flows into the input pipe portions at a constant time interval, an inflow boundary condition of the virtual exhaust gas at an input of the input pipes, and an outflow boundary condition of the virtual exhaust gas at an output of the converged pipe portion; determining any of two cylinders in the plurality of cylinders to be a first specific cylinder and a second specific cylinder, the input pipe portion connected to the first specific cylinder to be a first specific input portion and the input pipe portion connected to the second specific cylinder to be a second specific input portion; dividing the area of the exhaust pipe into a plurality of finite elements; setting, when calculating transfer of the virtual exhaust gas between the finite elements, identification information to mutually identify a virtual exhaust gas flowing into the finite elements of the first specific input pipe portion from the first specific cylinder, a virtual exhaust gas flowing into the finite elements of the second specific input pipe portion from the second specific cylinder, a virtual exhaust gas flowing into the finite elements of the rest of input pipe portions excluding the first and second specific input pipe portions from the rest of the cylinders excluding the first and second specific cylinders; calculating a first analysis amplitude curve representing a change in concentration of a first virtual exhaust gas with time at an observation finite element in the observation point of the converged pipe portion, the first virtual exhaust gas being exhausted from the first specific cylinder to the exhaust pipe, a second analysis amplitude curve representing a change in concentration of a second virtual exhaust gas with time at an observation finite element in the observation point of the converged pipe portion, the second virtual exhaust gas being exhausted from the second specific cylinder to the exhaust pipe, and an analysis time interval representing a time interval from a reference point in the first analysis amplitude curve to a reference point in the second analysis amplitude curve; setting, when obtaining the measurement data, an air-fuel ratio of the rest of the cylinders excluding the first specific cylinder to be within a predetermined range and an air-fuel ratio of the first specific cylinder to be beyond the predetermined range; measuring, for the exhaust gas exhausted to the exhaust pipe from the first specific cylinder during a combustion operation of the internal combustion engine, a change in the specific gas component with time at the observation point of the converged pipe portion, thereby obtaining a first actual amplitude curve; setting, when obtaining the measurement data, an air-fuel ratio of the rest of the cylinders excluding the second specific cylinder to be within a predetermined range and an air-fuel ratio of the second specific cylinder to be beyond the predetermined range; measuring, for the exhaust gas exhausted to the exhaust pipe from the second specific cylinder during a combustion operation of the internal combustion engine, a change in the specific gas component with time at the observation point of the converged pipe portion, thereby obtaining a second actual amplitude curve; combining the first actual amplitude curve and the second actual amplitude curve when zero points between the first and second amplitude curves are aligned, and obtaining, as an actual time interval, a time interval from a reference point of the first actual amplitude curve to a reference point of the second actual amplitude curve; and determining that the analysis data is valid, when a difference between the analysis time interval and the actual time interval is within a predetermined correlation range.

A yet another aspect of the present disclosure is a method for evaluating an exhaust gas simulation, in which a computer simulation based on a fluid dynamics analysis and an actual measurement are applied to an exhaust gas flow which is a flow of an exhaust gas in an exhaust pipe of an internal combustion engine so as to obtain an analysis data and a measurement data respectively, the exhaust pipe having a converged pipe portion in which a plurality of input pipe portions are converged and a catalyst is disposed, the input pipe portions being respectively connected to a plurality of cylinders of the internal combustion engine; the computer simulation and the actual measurement are applied to the exhaust gas in the converged pipe portion, and the analysis data and the measurement data are compared, thereby evaluating a validity of the analysis data.

The method including steps of: setting, in the analysis data, various conditions including a three-dimensional shaped model of the exhaust pipe, a physical property of a virtual exhaust gas, an inflow time interval of the virtual exhaust gas between the plurality of cylinders in which the virtual exhaust gas successively flows into the input pipe portions at a constant time interval, an inflow boundary condition of the virtual exhaust gas at an input of the input pipes, and an outflow boundary condition of the virtual exhaust gas at an output of the converged pipe portion; determining any of cylinders in the plurality of cylinders to be a specific cylinder and the input pipe portion connected to the specific cylinder to be a specific input portion; dividing the area of the exhaust pipe into a plurality of finite elements; setting, when calculating transfer of the virtual exhaust gas between the finite elements, identification information to mutually identify each of virtual exhaust gasses flowing into respective finite elements corresponding to a plurality of input pipe portions from respective cylinders; calculating, for the respective cylinders, analysis amplitude curves representing a change in concentration of the virtual exhaust gasses with time at an observation finite element in the observation point of the converged pipe portion, the virtual exhaust gasses being exhausted from the respective cylinders to the exhaust pipe, and analysis time intervals representing time intervals between mutually adjacent reference points in the analysis amplitude curves for respective cylinders; setting, in the measurement data, an air-fuel ratio of the rest of the cylinders excluding a specific cylinder selected from the plurality of cylinders to be within a predetermined range and an air-fuel ratio of the specific cylinder to be beyond the predetermined range; measuring, for the exhaust gas exhausted to the exhaust pipe from the specific cylinder during a combustion operation of the internal combustion engine, a change in the specific gas component with time at the observation point of the converged pipe portion, and determining the change in the specific gas component as actual amplitude curves; measuring the actual amplitude curves for respective cylinders under a condition that each of the cylinders is sequentially set as the specific cylinder; combining the measured actual amplitude curves when zero points between the measured actual amplitude curves are aligned, and obtaining, as actual time intervals for respective cylinders, time intervals between mutually adjacent reference points in the measured actual amplitude curves for respective cylinders; and determining that the analysis data is valid, when a difference between the analysis time interval and the actual time interval for respective cylinders is within a predetermined correlation range.

According to each of the exhaust gas simulation evaluation methods comparing the analysis data obtained by a simulation based on fluid dynamics analysis and the actual measurement data by actual equipment, a completely new measure is utilized to evaluate the validity of the analysis data. Note that fluid dynamics analysis is also referred to as computational fluid dynamics (CFD).

The above-mentioned measure employs an analysis time interval that represents a time at which the exhaust gas exhausted from the cylinders of the internal combustion engine reaches an observation point in the converged pipe portion of the exhaust pipe, and an actual measurement time interval thereof. Also, according to the exhaust gas simulation evaluation, methods of measuring concentration of specific gas component of the exhaust gas are considered.

The first aspect of the present disclosure will be described.

In the analysis data, various conditions are set as analysis conditions, the area of the exhaust pipe is divided into a plurality of finite elements, and transfer of the virtual gasses between the finite elements are calculated. At this time, a specific input pipe portion connected to a specific cylinder used for the evaluation is determined, and identification information is set which is capable of identifying a virtual exhaust gas flowing into the specific input pipe portion and a virtual exhaust gas flowing into the rest of input pipe portions. The inflow time interval in the analysis data is set as same as a time interval between respective cylinders of the actual internal combustion engine, where any combustion stroke such as combustion, exhaust or the like is sequentially executed in the combustion cycle. For a fluid used in the analysis data, its gas component is not considered. Hence, the fluid is referred to as a virtual exhaust gas.

For a virtual exhaust gas exhausted to the exhaust pipe from the specific cylinder, a change in concentration of the virtual exhaust gas with time at an observation finite element in the observation point of the converged pipe portion is determined as an analysis amplitude curve. The concentration of the virtual exhaust gas at the observation point in the converged pipe portion are repeatedly increased/decreased in response to the combustion cycle of the specific cylinder of the internal combustion engine. Subsequently, a time interval from the zero point relative to the time course in the simulation to the reference point in the analysis amplitude curve is determined as an analysis time interval. The reference point in the analysis amplitude curve is defined as a peak point, a bottom point, or any point between the peak point and the bottom point. The zero point relative to the time course in the simulation is set as, for example, a crank angle of the crank shaft of the internal combustion engine, a start point of the combustion cycle of the specific cylinder or the like, which is the same as the zero point relative to the time course in the actual measurement.

On the other hand, when obtaining actual measurement data, combustion operation of the internal combustion engine is performed under the condition where the air/fuel ratio of the cylinders excluding the specific cylinder is set within a predetermined range, and the air/fuel ratio of the specific cylinder is set beyond the predetermined range. At this time, for the exhaust gas exhausted to the exhaust pipe from the specific cylinder during a combustion operation of the internal combustion engine, a change in the specific gas component with time at the observation point of the converged pipe portion is measured, thereby obtaining an actual amplitude curve. The concentration of the specific gas component at the observation point in the converged pipe portion increases/decreases in response to the combustion cycle of the specific cylinder of the internal combustion engine. Next, a time interval from the zero point relative to the time course in the actual measurement to the reference point in the actual amplitude curve is determined as an actual time interval. The reference point in the actual amplitude curve is defined as the same as that of the analysis amplitude curve, i.e., a peak point, a bottom point, or any point between the peak point and the bottom point.

Thereafter, the analysis data is determined as valid when the difference between the analysis time interval and the actual time interval is within a predetermined correlation range. The lengths of each input pipe portions and the converged pipe portion, a cross-sectional area, a cross-sectional shape, entire shape of the exhaust pipe 2, influence the velocity distribution and the concentration distribution of the exhaust gas in the converged pipe portion. The analysis time interval and the actual time interval are calculated or measured as a value offset from the inflow time interval set in the analysis data, reflecting a change in the concentration of the virtual exhaust gas or the concentration of the specific gas component over time.

Accordingly, by checking the analysis time and the actual time intervals and comparing them, it is confirmed whether or not the velocity distribution and the concentration distribution of the exhaust gas in the converged pipe portion of the actual equipment are reflected to the velocity distribution and the concentration distribution of the exhaust gas in the converged pipe portion according to the simulation. Hence, the process can determine that the analysis data of the simulation expresses correct velocity distribution and the concentration distribution of the exhaust gas in the converged pipe portion with a predetermined accuracy, when the difference between the analysis time interval and the actual time interval is within a predetermined correlation range.

As for operational effects, in the analysis data, the process can determine from which cylinder the virtual exhaust gas that reaches the observation point in the converged pipe portion is exhausted. On the other hand, in the actual data, in order to determine a cylinder from which the exhaust gas is exhausted and reached to the observation point of the converged pipe portion, a special method is required. Accordingly, when calculating the actual measurement time interval in the actual measurement data, the air/fuel ratio of the specific cylinder and the air/fuel ratio of the rest of cylinders are set to be different from each other. The difference between the air/fuel ratios influences the concentration of specific gas components contained in the exhaust gas, such as NOx (nitrogen oxides), CO (carbon monoxide), HC (hydrocarbon), oxygen or the like. Therefore, a change in concentration of the specific gas component in the exhausted gas over time, which is actually measured at the observation point in the converged pipe, can be identified as a change in the CO concentration over time, which is contained in the exhausted gas exhausted from the specific cylinder.

Thus, in the actual equipment of the internal combustion engine, substantially, an actual time interval can be calculated based on the actual amplitude curve that represents a change in the concentration of the exhaust gas over time, which is exhausted from the specific cylinder. Hence, the analysis time interval calculated for the specific cylinder and the actual time interval can be compared accurately.

The result of the simulation based on the computational fluid dynamics analysis using the analysis computer is appropriately evaluated by using the actual equipment. However, evaluation method thereof has not been established. According to the evaluation method of the exhaust gas simulation of the present embodiment, a target of the simulation is specific, that is, a gas flow of the exhaust gas in the converged pipe portion of the exhaust pipe of the internal combustion engine. In this respect, by focusing a fact that the internal combustion engine has a plurality of cylinders and the exhaust gas is sequentially exhausted to the cylinders, a state of the exhaust gas in any of the cylinders is set to be different from a state of the exhaust gas in the rest of the cylinders, and a change in the concentration of the specific gas component is observed for the exhaust gas exhausted from any of the cylinders. Thus, the result of simulation can be simply and appropriately evaluated or verified by using the actual equipment.

In the evaluation method for exhaust gas according to another aspect of the present disclosure, instead of calculating the time interval between the zero point of the time course and the reference point of the amplitude curve, a time interval between the reference points in the amplitude curves of two cylinders is calculated. Then, the time interval calculated based on the concentration of the virtual exhaust gas of the two cylinders, and the actual time interval calculated based on the concentration of the virtual exhaust gas of the two cylinders are compared, thereby evaluating the validity of the analysis data. According to another aspect of the present disclosure, amplitude curves for two cylinders are considered, thereby further improving the accuracy for evaluating the analysis data. Other configurations of another aspect pf the present disclosure are the same as that of one aspect of the present disclosure so that similar effects thereof can be obtained.

In the evaluation method for exhaust gas according to yet another aspect of the present disclosure, instead of calculating the time interval between the zero point of the time course and the reference point of the amplitude curve or the time interval between the reference points in the amplitude curves of two cylinders, a time interval between the reference points of the amplitude curves for all cylinders is calculated. Then, by comparing the analysis time intervals calculated based on concentration of the virtual exhaust gas for all cylinders, and the actual time intervals calculated based on concentration of the specific gas component of the virtual exhaust gas for all cylinders, thereby evaluating the validity of the analysis data. According to yet another aspect of the present disclosure, since the all cylinders are considered, the validity of the analysis data can be evaluated more accurately. Other configurations of another aspect pf the present disclosure are the same as that of one aspect of the present disclosure so that similar effects thereof can be obtained.

Therefore, according to the above-described each evaluation method for exhaust gas simulation, the validity of the analysis data produced by the simulation can be evaluated readily and appropriately.

In each of the evaluation methods of the exhaust gas simulation of the aspects, differentiating the air/fuel ratios when actually measuring measurement data means differentiating the mixing ratio of the air and the fuel. Hence, air/fuel ratio can be understood as a value obtained by dividing actual air/fuel ratio in the internal combustion engine by the theoretical air/fuel ratio, which is referred to as excess air factor.

Reference signs in parenthesis of the elements in one aspect of the present disclosure refer to correspondence of reference signs in drawings of the embodiments. However, these reference signs do not limit to contents of the embodiments corresponding to each element.

DETAILED DESCRIPTION OF THE PREFERRED EMBODIMENTS

With reference to the drawings, preferred embodiments of the above-described a method for evaluating exhaust gas simulation will be described.

First Embodiment

Figure 1:
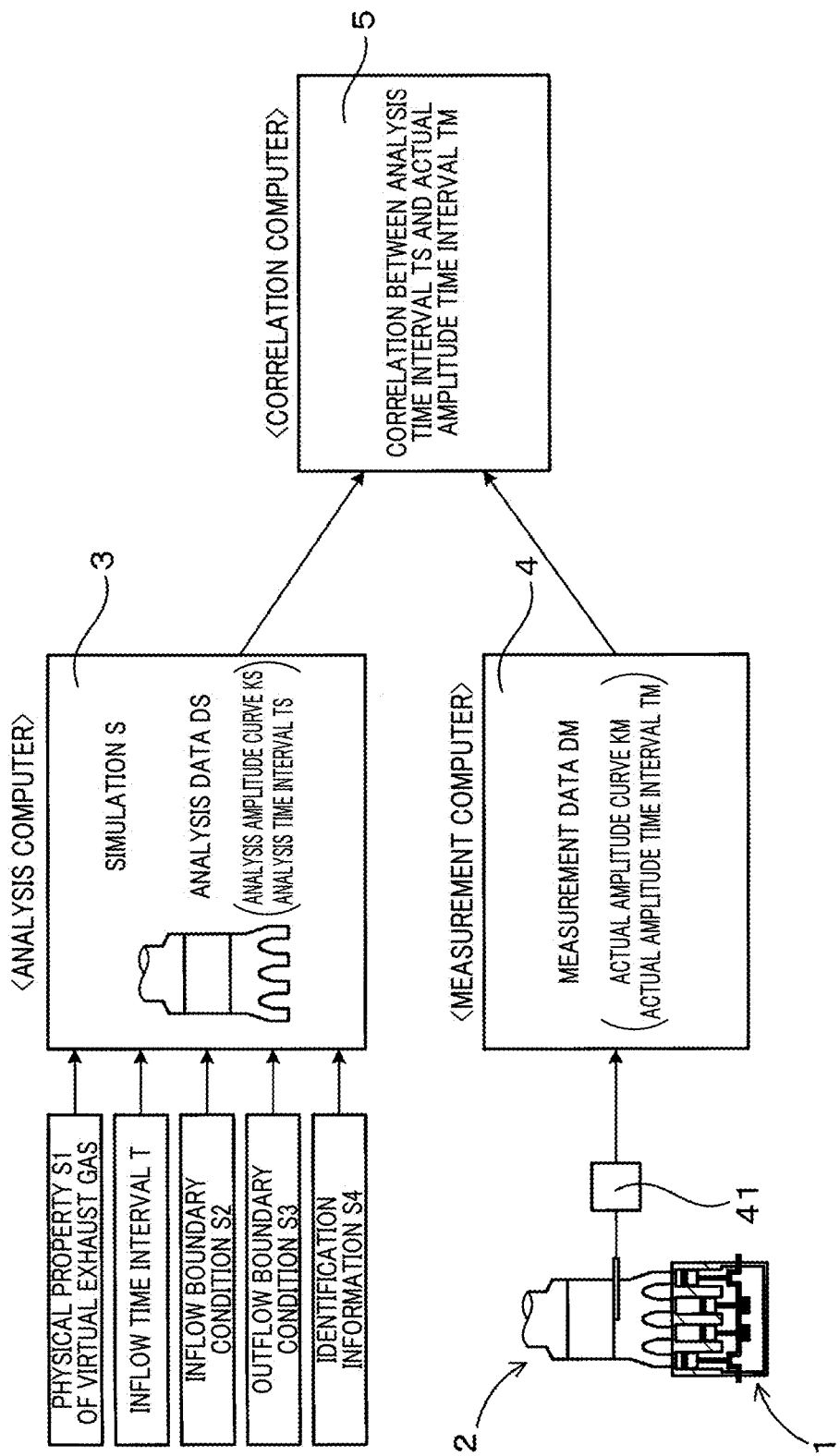
FIG. 1 is an explanatory diagram showing an overall evaluation method of exhaust gas simulation according to a first embodiment of the present disclosure.
Figure 2:
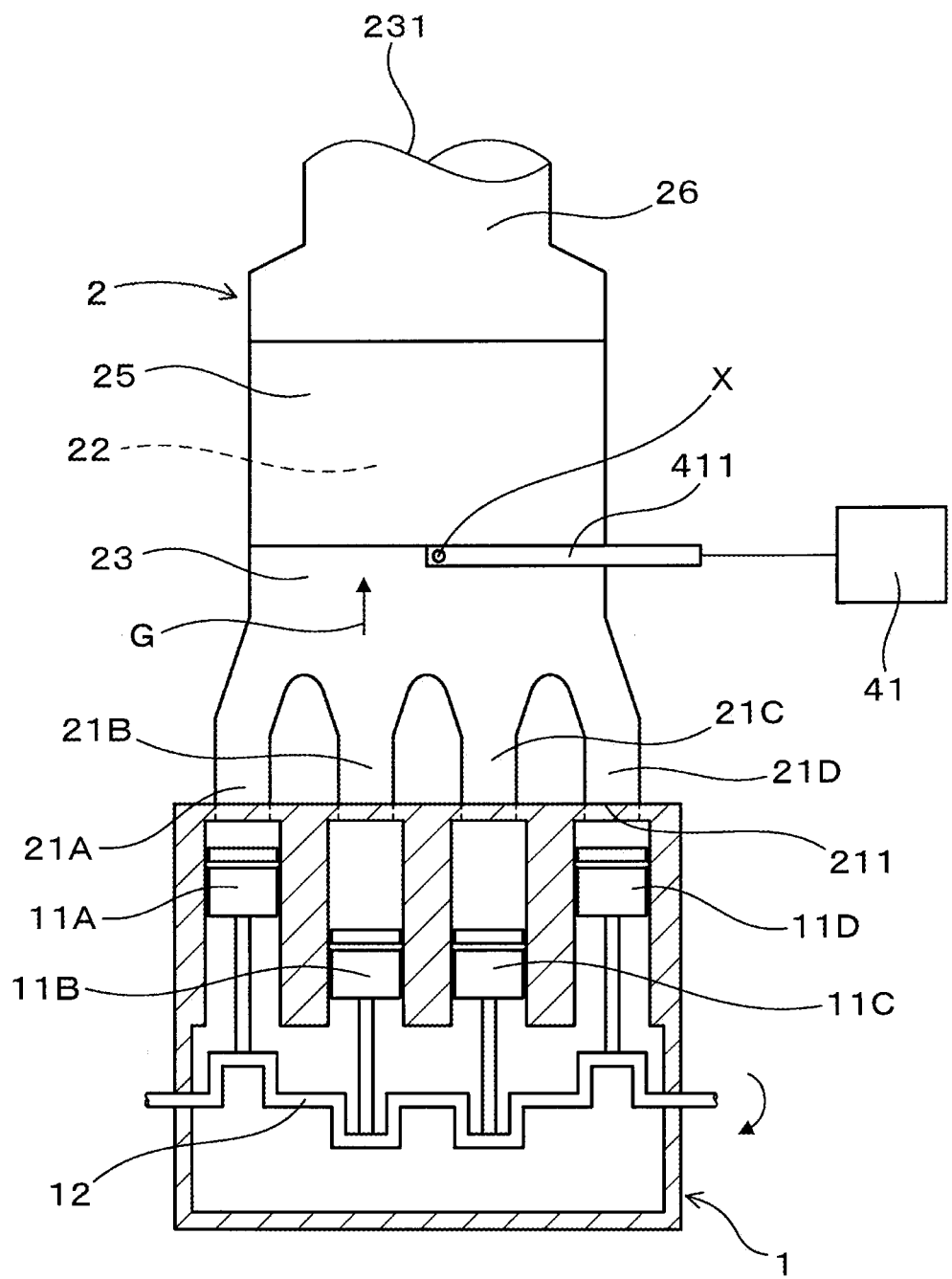
FIG. 2 is an explanatory diagram showing an internal combustion engine and an exhaust pipe according to the first embodiment.

As shown in FIGS. 1 and 2, a method for evaluating exhaust gas simulation (hereinafter referred to as evaluation method of exhaust simulation) is performed for a gas flow of an exhaust gas G in the exhaust pipe 2 of an internal combustion engine 1. Specifically, analysis data DS is obtained by a simulation S executed on an analysis computer 3 based on the computational fluid dynamics (CFD) analysis, and actual measurement data DM is actually measured during combustion operation in the internal combustion engine 1, then the analysis data DS and the actual measurement data are compared to evaluate the validity of the analysis data DS. As shown in FIG. 2, the exhaust pipe 2 of the internal combustion engine 1 is provided with a plurality of input pipes 21A, 21B, 21C and 21D which are connected to a plurality of cylinders 11A, 11B, 11C and 11D of the internal combustion engine 1 respectively, and a converged pipe portion 23 in which the input pipes 21A, 21B, 21C and 21D are converged and a catalyst 22 is disposed. The analysis data DS is produced by analyzing the flow of a virtual exhaust gas Gs in the converged pipe portion 23 of the exhaust pipe 2. The actual measurement data DM is produced by measuring the flow of the exhaust gas G in the converged pipe portion 23 of the exhaust pipe 2.

Figure 3:
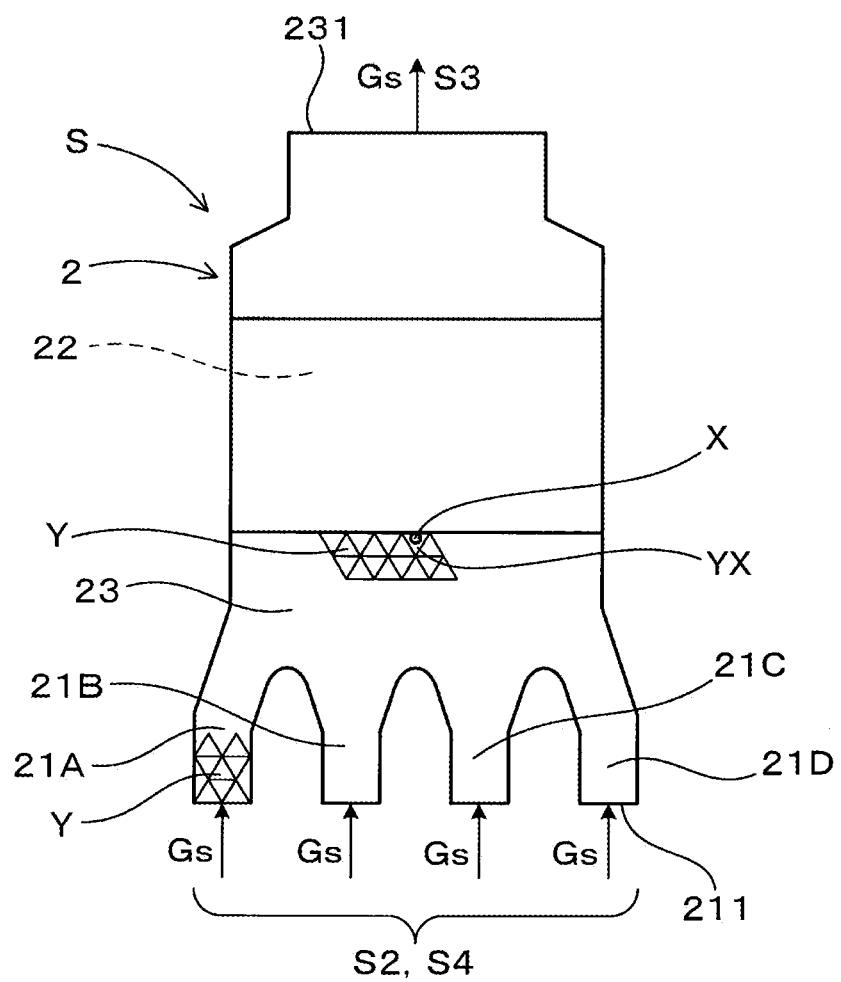
FIG. 3 is an explanatory diagram showing an internal combustion engine and an exhaust pipe on the simulation according to the first embodiment.

For the analysis data DS, as shown in FIGS. 1 and 3, various conditions are set including a three-dimensional shaped model of the exhaust pipe 2, a physical property value S1 of a virtual exhaust gas Gs, an inflow time interval T of the virtual exhaust gas Gs between cylinders 11A, 11B, 11C, 11D, in which the virtual exhaust gas Gs successively flows into the input pipes 21A, 21B, 21C and 21D at a constant time interval, an inflow boundary condition S2 of the virtual exhaust gas Gs at the input 211 of the input pipes 21A, 21B, 21C and 21D, and an outflow boundary condition S3 of the virtual exhaust gas GS at the output 231 of the converged pipe portion 23. Also, one of the cylinders 11A, 11B, 11C and 11D is determined as a specific cylinder and an input pipe connected to the specific cylinder is defined as a specific input pipe.

Figure 4:
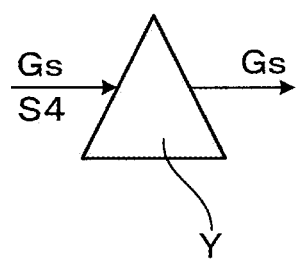
FIG. 4 is an explanatory diagram showing a finite element of the simulation according to the first embodiment.
Figure 5:
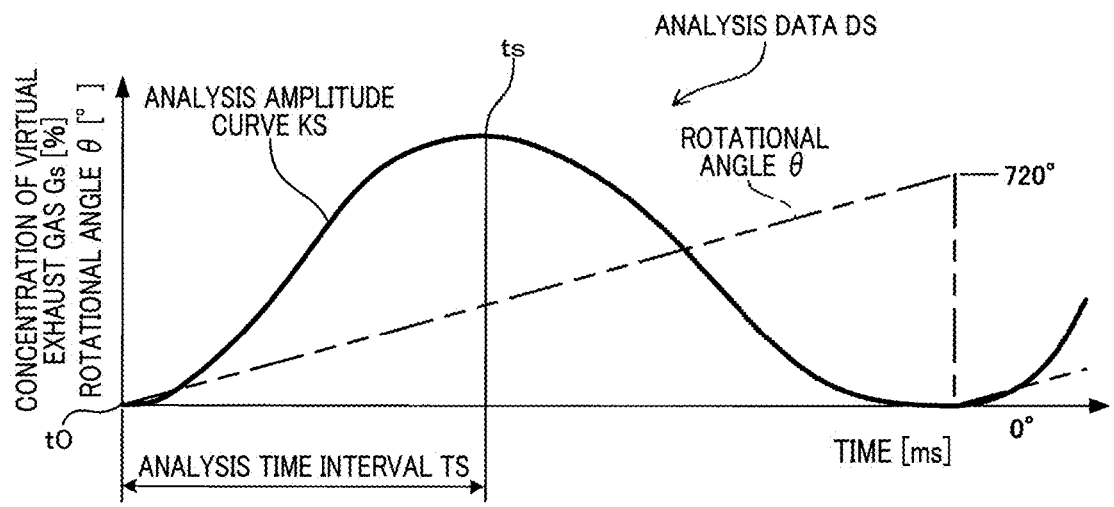
FIG. 5 is a graph showing a change in a virtual exhaust gas concentration and a rotational angle of a crank shaft in the analysis data according to the first embodiment.

Moreover, as shown in FIGS. 3 and 4, the area of the exhaust pipe 2 is divided into a plurality of finite elements Y, and identification information S4 is set to identify the virtual exhaust gas Gs flowing into the finite elements Y of the specific input pipe from the specific cylinder, and the virtual exhaust gas Gs flowing into the finite elements Y of the rest of input pipes excluding the specific input pipe from the rest of the cylinders excluding the specific cylinder, when calculating transfer of the virtual exhaust gas Gs between the finite elements Y. Then, as shown in FIGS. 1 and 5, an analysis amplitude curve KS and an analysis time interval TS are calculated. The analysis amplitude curve KS represents a change in concentration of the virtual exhaust gas Gs with time at an observation finite element YX in the observation point X of the converged pipe portion 23, which is exhausted to the exhaust pipe 2 from the specific cylinder. The analysis time interval TS represents a time interval from a zero point t0 relative to the time course during the simulation S to the reference point is in the analysis amplitude curve KS.

Figure 6:
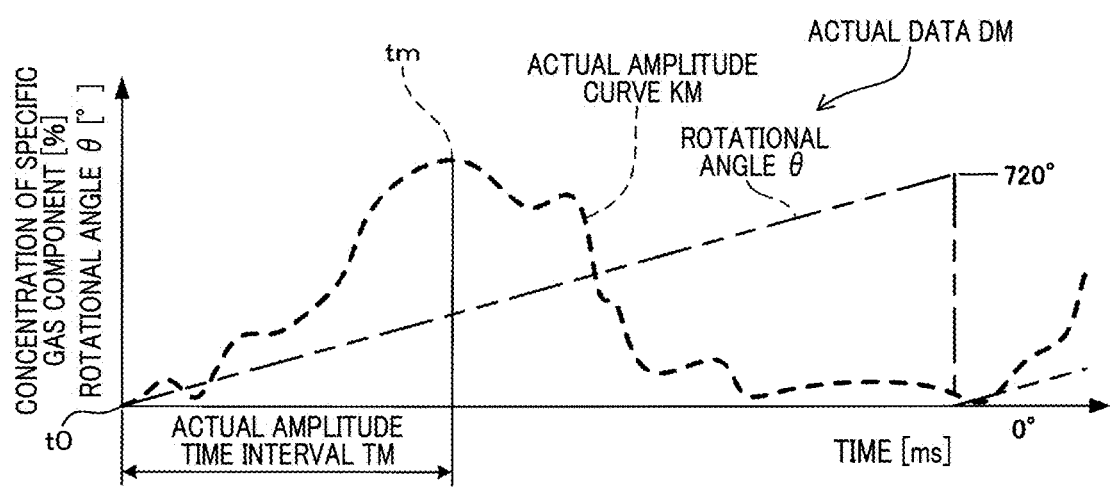
FIG. 6 is a graph showing a change in a gas concentration of a specific gas in the exhaust gas and a rotational angle of the crank shaft in the actual measurement data according to the first embodiment.

In the actual measurement data DM, as shown in FIGS. 1,2 and 6, the air-fuel ratio of the rest of the cylinders excluding the specific cylinder is set within a predetermined range and the air-fuel ration of the specific cylinder is set beyond the predetermined range. When in a combustion operation of the internal combustion engine 1, for the exhaust gas G exhausted to the exhaust pipe 2 from the specific cylinder, a change in the specific gas component with time is actually measured at the observation point of X of the converged pipe 23, thereby obtaining an actual amplitude curve KM. Also, a time interval between the zero point t0 in the actual measurement to the reference point tm in the actual amplitude curve KM is calculated to obtain the actual time interval TM. Thereafter, the process determines that the analysis data DS for the flow of the exhaust gas G in the converged pipe 23 of the exhaust pipe 2 is valid, when the difference between the analysis time interval TS and the actual time interval TM is within a predetermined correlation range.

Hereinafter, an evaluation method of the exhaust gas simulation according to the present embodiment will be described in detail. As shown in FIG. 1, the evaluation method of the exhaust gas simulation uses actual measurement data DM of the actual equipment so as to evaluate the analysis data DS of the simulation S of the analysis computer 3. Then, when the actual measurement data DM and the analysis data DS are within a predetermined correlation range, it is determined that the simulation S based on the computational fluid dynamics analysis in the analysis computer 3 has a predetermined accuracy. Hence, in the case where the simulation S is determined as valid for the exhaust gas flow G in the exhaust pipe 2 of a typical internal combustion engine 1, the result of the simulation S is reliable and can be used for designing the exhaust pipe 2. Thus, although without obtaining the actual measurement data DM by using the actual equipment after designing the exhaust pipe 2, from the result of the simulation S, the exhaust gas flow G in the exhaust pipe 2 can be estimated with a certain accuracy.

As shown in FIG. 2, the internal combustion engine 1 can be a reciprocating engine, a rotary engine, a hybrid engine or the like. The internal combustion engine 1 can be a four stroke-engine or a two stroke-engine. The number of cylinders of the internal combustion engine may be set to 2 to 14 cylinders. The exhaust pipe 2 is provided with an exhaust manifold 24 coupled to the internal combustion engine 1, a catalyst converter 25 coupled to a downstream side in the gas flow of the exhaust gas G, and an exhaust pipe 26 coupled to further downstream side thereof than the position of the catalyst converter 2.

In the simulation S, objects of the exhaust pipe 2 from which the analysis data DS is generated, may be the exhaust manifold 24 and the catalyst converter 25, and the exhaust manifold 24, the catalyst converter 25 and the exhaust pipe 26. The exhaust manifold 24 is configured of a plurality of input pipes 21A, 21B, 21C and 21D and the converged pipe portion 23. The catalyst converter 25 and the exhaust pipe 26 are configured of the converged pipe 23.

[Configuration of Simulation S and Generation of Analysis Data DS]

The simulation S can be provided as a software operated on an operation system of the analysis computer 3. The CFD analysis used for the simulation S according to the present embodiment includes an analysis of the flow of the exhaust gas G based on the finite volume method. The method used for the CFD analysis includes finite differential method, finite element Y method and the like, other than the finite volume method. The finite volume method has both features of the finite differential method and the finite element method, and thus suitable for the CFD analysis. The finite volume method may also be referred to as numerical fluid dynamics analysis.

For the software for the simulation according to the present embodiment, Star-CCM+ of Siemens is employed. Other than this software, ANSYS FLUENT produced by ANSYS, Inc., icon-CFD produced by IDAJ Co., LTD., STREAM produced by Software Cradle Co., Ltd, PHOENICS produced by Concentration Heat and Momentum Limited or the like can be employed.

According to the simulation S using the finite volume method, Navier-Stokes equation, equation of continuity, equation of energy or the like are used to calculate the transfer of the virtual exhaust gas Gs, for the plurality of finite elements Y in the exhaust pipe 2. The Navier-Stokes equation is expressed as, for example, $\rho\{\partial V/\partial t+\nabla\cdot(v\,v)\}=-\nabla p+\nabla\cdot(2\mu D)$. The equation of continuity is expressed as, for example, $\nabla\cdot v=0$. The equation of energy is expressed as, for example, $\partial(\rho CT)/\partial t+\nabla\cdot(v\rho CT)=\nabla\cdot(k\nabla T)$.

Here, $\partial$ (der) represents partial derivative of multivariable function, and $\nabla$ nebula represents the operator for vector analysis. Also, $\rho$ represents concentration, v represents velocity of the flow, t represents time, $\mu$ represents viscosity coefficient, D represents deformation velocity tensor, C represents specific heat, T represents temperature, and k represents thermal conductivity.

In the simulation S, when calculating transfer of the virtual exhaust gas Gs between the finite elements Y, various conditions are set for respective equations in the finite volume method. The physical property value S1 of the includes the concentration of the virtual exhaust gas Gs, the viscosity coefficient, the specific heat, the thermal conductivity, and the temperature. The virtual exhaust gas Gs is defined such that the exhaust gas G is treated as a virtual fluid without considering the content of the gas. The virtual exhaust gas Gs according to the present embodiment is treated as incompressible fluid for making the calculation simple. However, the virtual exhaust gas may be treated as compressible gas.

Figure 7:
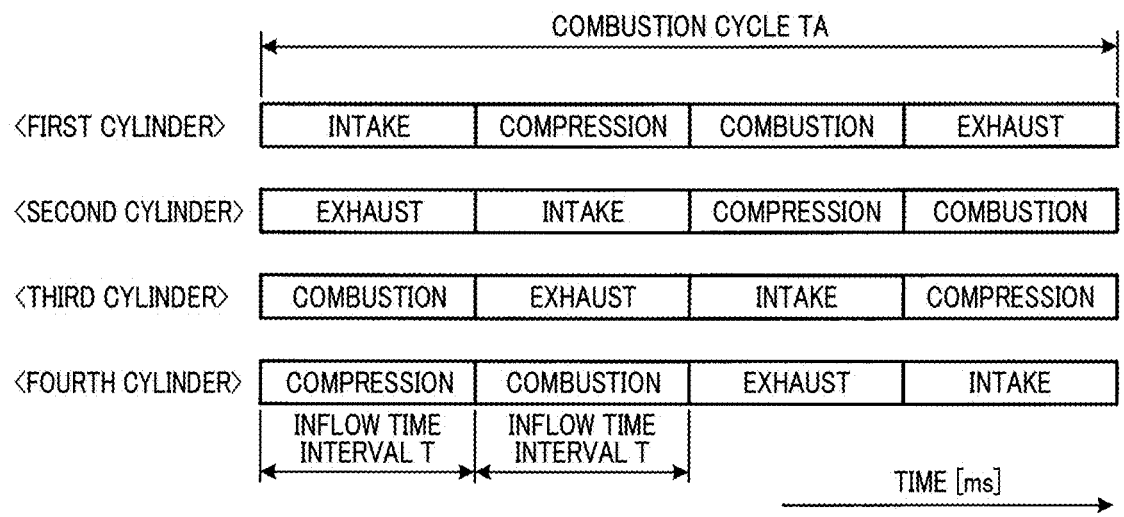
FIG. 7 is an explanatory diagram showing a combustion cycle of the internal combustion engine according to the first embodiment.

As shown in FIG. 7, the inflow time interval T is defined as an interval where exhaust stroke or the like is sequentially performed between the cylinders 11A, 11B, 11C and 11D. According to the internal combustion engine 1 is four stroke engine, in which the time interval between an intake stroke, a compression stroke, a combustion stroke and an exhaust stroke in the combustion cycle Ta of the cylinders 11A, 11B, 11C and 11D, depends on a rotational angle $\theta$ of the crank shaft 12. The crank shaft rotates by 720° for four strokes. The inflow time interval T is equivalent to the time interval when the crank shaft 12 rotates by 180°.

The inflow boundary condition S2 of the virtual exhaust Gs at the input 211 of the input pipes 21A, 21B, 21C and 21D is given as a flow velocity (amount of flowing) or pressure of the virtual exhaust gas Gs at the input 211 of respective input pipes 21A, 21B, 21C and 21D. The outflow boundary condition S3 of the virtual exhaust gas Gs at the output 231 of the converged pipe portion 23 is given as a flow velocity (amount of velocity) or pressure of the virtual exhaust gas Gs at the output 231 of the converged pipe portion 23. The output 231 of the converged pipe portion 23 can be set at an appropriate position in an upstream side or a downstream side of the catalyst 22 disposed in the converged pipe portion 23, other than the most downstream end of the converged pipe 23.

Various conditions when calculating the analysis data DS are compared with respective values when acquiring the actual measurement data DM, where the various conditions includes physical property value S1 such as the concentration, viscosity coefficient, the specific heat, the thermal conductivity and the temperature, the inflow time interval T of the virtual between the cylinders 11A, 11B, 11C and 11D, the flow velocity or the pressure of the virtual exhaust gas Gs at the input 211 of respective input pipes 21A, 21B, 21C and 21D, and the flow velocity or pressure of the virtual exhaust gas Gs at the output 231 of the converged pipe portion 23.

As shown FIGS. 3 and 4, the finite elements Y are also referred to as a mesh in which three-dimensional shape model of the exhaust pipe 2 is discretized when performing the simulation S on the analysis computer 3. When the number of finite elements Y increases, the accuracy of the simulation S increases but, longer time is required for the calculation. In the simulation S, transfer of the virtual exhaust gas Gs between finite elements Y is calculated based on a difference between a state of the virtual exhaust gas Gs flowing into the finite elements Y and a state of the virtual exhaust gas Gs flowing out from the finite elements Y. FIG. 3 roughly illustrates a part of the finite elements Y.

The identification information S4 is used to distinguish an exhaust gas G exhausted to the specific input pipe from the specific cylinder which is any one of the cylinders 11A, 11B, 11C and 11D, from an exhaust gas G exhausted to the rest of the input pipes from the rest of the cylinders. The specific cylinder and the specific input pipe may be selected from any of the cylinders 11A, 11B, 11C and 11D, and any of the input pipes 21A, 21B, 21C and 21D.

The identification information S4 is set such that data is added to the virtual exhaust gas Gs in the simulation S. The identification information S4 is added to the finite elements Y existing in the positions at which the virtual exhaust gas Gs flows into the input pipes 21A, 21B, 21C and 21D from the cylinders 11A, 11B, 11C and 11D, and sequentially kept at respective finite elements Y of the input pipe and the converged pipe positioned in downstream side of the flow of the virtual exhaust gas Gs than the finite elements Y to which the identification information S4 is added. Specifically, in the respective finite elements Y of the converged pipe portions, the virtual exhaust gas Gs flowing into the respective finite elements Y is identified whether the source of the virtual exhaust gas Gs belongs to which cylinder and which input pipe. Also, the virtual exhaust gas Gs from the plurality of cylinders 11A, 11B, 11C and 11D are mixed through the input pipes and flows into the respective finite elements Y. In this case, taking the ratio of the flow between the virtual exhaust gasses Gs of which the sources are different into consideration, the transfer of the virtual exhaust gas Gs between the finite elements Y is calculated.

As shown in FIG. 2, the exhaust gas G is exhausted to the exhaust pipe 2 sequentially from the cylinders 11A, 11B, 11C and 11D of the internal combustion engine 1. A concentration distribution appears at the observation point X, in which amount of exhausted gasses G which reach the observation point X are represented corresponding to respective cylinders. In particular, according to the present embodiment, the concentration distribution is observed for the exhaust gas G that reaches the observation point X of the converged pipe portion 23 from the specific cylinder. The exhaust gasses G exhausted from the cylinders 11A, 11B, 11C and 11D sequentially flowing into the input pipes 21A, 21B, 21C and 21D, pass sequentially through the converged pipe portion 23 while being mixed from each other. The concentration of the exhaust gasses G exhausted from the respective cylinders 11A, 11B, 11C and 11D change over time, which are observed at any observation point X in the converged pipe portion 23. The observation point X of the converged pipe portion 23 can be set at any point in the converged pipe portion 23.

The input pipes 21A, 21B, 21C and 21D of the exhaust manifold 24 are connected to a plurality of cylinders 11A, 11B, 11C and 11D of the internal combustion engine 1, respectively. Depending on positions in the vehicle or the like, where the internal combustion engine 1 and the exhaust pipe 2 are installed, and the way of installing them, the lengths and shapes of the input pipes 21A, 21B, 21C and 21D are likely to be different from each other. The specific cylinder used for analysis data DS and the specific cylinder of the actual measurement data DM are determined by identifying which position the cylinder is present in the cylinders 11A, 11B, 11C and 11D of the internal combustion engine 1.

As shown in FIG. 3, when calculating the analysis data DS in the simulation S, the inflow time interval T in the analysis data DS is set to be the same as a time interval during which a combustion or an exhaust stroke in the combustion cycle TA is performed between cylinders of actual equipment of the internal combustion engine 1. Moreover, when calculating the analysis data DS, a finite element Y positioned at an observation point X in the converged pipe portion 23 is selected as an observation finite element YX. Also, as shown in FIG. 5, a change in a concentration of the virtual exhaust gas Gs which is a concentration of the specific virtual exhaust gas Gs at the observation finite element YX is plotted as an analysis amplitude curve KS, when it is assumed that the virtual exhaust gas Gs exhausted to the exhaust pipe 2 from the specific cylinder to be the specific virtual exhaust gas Gs. The concentration of the virtual exhaust gas Gs is expressed as a concentration of the specific virtual exhaust gas Gs that occupies the observation finite element YX positioned at the observation point X of the converged pipe portion 23. Also, the concentration of the virtual exhaust gas Gs can be expressed as a volume ratio of the specific virtual exhaust gas Gs to the whole virtual exhaust gas Gs at the observation point X. The analysis amplitude curve KS is defined as a curve in which an amplitude representing the concentration of the virtual exhaust gas Gs repeatedly increases and decreases in response to the combustion cycle TA.

The zero point t0 in the time course during the simulation S can be set as any specific rotational angle θ, where the rotational angle θ of the crank shaft 12 of the internal combustion engine 1 rotates by 720° in the one cycle. The zero point t0 according to the present embodiment is defined as a time at which the rotational angle θ of the crank shaft angle is 0°. The zero point t0 in the time course in the simulation S and the zero point t0 in the time course in the actual measurement are synchronized by using the rotational angle θ of the crank shaft 12.

As shown in FIG. 5, the reference point ts in the analysis amplitude curve KS according to the present embodiment is defined as a peak of the analysis amplitude curve KS at which the concentration of the virtual exhaust gas Gs peaks. The reference point ts may be set as a bottom point of the analysis amplitude curve KS at which the concentration of the virtual exhaust gas Gs becomes minimum. Also, the reference point ts may be set as a time point at which the deviation becomes center value (50) in the standard deviation of the concentration distribution of the virtual exhaust gas Gs. Further, the reference point ts in the analysis amplitude curve KS may be set corresponding to the reference point tm in the actual measurement amplitude curve KM, where the value is shifted by a specific period from the peak point, the bottom point and the center of the deviation.

The analysis time interval TS used for the analysis data DS is calculated as a time interval between the zero point t0 in the time course and the reference point ts in the analysis amplitude curve KS. The time interval is defined reflecting the result of the simulation S calculated using the concentration and a change in the fluid velocity of the specific virtual exhaust gas Gs appearing at the observation point X of the converged pipe portion 23.

[Calculation of Actual Measurement Data DM]

As shown in FIG. 2, the actual measurement data DM is obtained by measuring the concentration of the specific gas component in the exhaust gas G exhausted to the exhaust pipe 2 during the combustion operation of the internal combustion engine 1. The "actual measurement" means that it is actually measured. The concentration of the specific gas component is used as follows. The air/fuel ratio of the specific cylinder is set to be different from the air/fuel ratio of the rest of the cylinders such that a change in the concentration of the specific gas component of the exhaust gas exhausted from the specific cylinder can be observed. The air/fuel ratio is referred to as a mixture ratio between amount of fuel and amount of air in the cylinders 11A, 11B, 11C and 11D of the internal combustion engine 1. The theoretical air fuel ratio is defined as a case where the mass of the fuel is 1 g and the mass of the air is 14.7 g, which allows the fuel and the air react with each other appropriately.

In the case where the air/fuel ratio is set to rich side in which an amount of the fuel is larger than that of the air compared to the theoretical air/fuel ratio, concentration of unburnt gas exhausted to the exhaust pipe 2 such as CO (i.e., carbon monoxide) and HC (i.e., hydrocarbon) become higher. On the other hand, in the case where the air/fuel ratio is set to the lean side in which an amount of the fuel is smaller than that of the air compared to the theoretical air/fuel ratio, concentration of NOx (nitrogen oxides), oxygen or the like which are exhausted to the exhaust pipe 2 becomes higher.

According to the present embodiment, when operating a combustion operation of the internal combustion engine 1, the air/fuel ratio of the specific cylinder and the air/fuel ratio of the rest of the cylinders are set to be different from each other such that the ratio of fuel supplied to the specific cylinder is set to be larger than the ratio of the fuel supplied to the rest of the cylinders. More specifically, the air/fuel ratio of the specific cylinder is set to be rich side and the air/fuel ratios of the rest of the cylinders are set to be the theoretical air/fuel ratio. The air/fuel ratio of the rest of the cylinders are set to be the same within a predetermined allowable error range. The allowable error range is defined as a case where an error of the air/fuel ratio is within ±5%. The concentration of the specific gas component which are actually measured is determined as CO concentration. Also, the concentration of the specific gas component which is actually measured may be HC concentration.

During a combustion operation of the internal combustion engine 1, the air/fuel ratio of the specific cylinder and the air/fuel ratio of the rest of the cylinders are set to be different from each other such that the ratio of fuel supplied to the specific cylinder is set to be smaller than the ratio of the fuel supplied to the rest of the cylinders. In this case, the air/fuel ratio of the specific cylinder can be set to the lean side and the air/fuel ratio of the rest of the cylinders can be set to the theoretical air/fuel ratio. In this case, the concentration of the specific gas component which are actually measured can be NOx concentration, oxygen concentration or the like. A predetermined range in which the air/fuel ratio of the specific cylinder is set and a predetermined range in which the air/fuel ratio corresponding to the rest of the cylinders are set, can be determined such that a change in the concentration of the specific gas component contained in the exhaust gas G significantly appears.

As shown in FIGS. 1 and 2, when acquiring the actual measurement data DM, a measurement probe 411 of a gas analyzer 41 that measures a specific gas component is disposed at the observation position X of the converged pipe portion 23 of the exhaust pipe 2. The data of the specific gas component measured by the gas analyzer 41 is stored in the measurement computer 4 as a control unit. When operating the combustion operation of the internal combustion engine 1, the CO concentration of the exhaust gas G exhausted from the specific cylinder in which the air/fuel ratio is set in rich side is higher than the CO concentration of the exhaust gas G exhausted from the rest of the cylinders. The exhaust gas from the cylinders 11A, 11B, 11C and 11D sequentially flow into the exhaust pipe 2, and when the exhaust gas G exhausted from the specific cylinder reaches the observation point X, the CO concentration measured by the gas analyzer 41 becomes high.

Then, the gas analyzer 41 measures concentration of the specific gas component at the observation position X of the converged pipe portion 23 at a predetermined sampling interval. Then, a change in the concentration of the specific gas component over time is stored in the measurement computer 4 as the actual amplitude curve KM. The actual amplitude curve KM is obtained as a curve which repeatedly increases or decreases the amplitude that represents amount of concentration of the specific gas component in the exhaust gas G in response to the combustion cycle TA. The measurement computer 4 may be different from the analysis computer 3 or the same as the analysis computer 3.

As shown in FIG. 6, the zero point t0 of the actual measurement can be set similar to the zero point t0 in the simulation S. Also, the zero point t0 is used as a reference point when comparing the actual measurement data DM with the actual equipment and the analysis data of the simulation S. Accordingly, these zero points t0 are set to be the same value as much as possible. Moreover, the reference point tm in the actual amplitude curve KM can be set similar to the reference point is in the analysis amplitude curve KS.

The actual measurement time interval TM used as the actual measurement data DM is calculated as a time interval from the actual measurement zero point t0 to the reference point tm in the actual amplitude curve KM. The actual measurement time interval TM changes depending on the concentration and the flow velocity of the specific gas component which appears at the observation point X of the converged pipe portion 23.

When actually measuring concentration of the specific gas component in the internal combustion engine 1, the flow velocity or the pressure of the exhaust gas G as the virtual exhaust gas Gs at the input 211 of the input pipes 21A, 21B, 21C and 21D which are used for calculating the analysis data DS, and the flow velocity or the pressure of the exhaust gas G as the virtual exhaust gas GS at the output 231 of the converged pipe portion 23 which are used for calculating the analysis data DS, are actually measured or calculated. The flow velocity or the pressure of the exhaust gas G can be simply obtained by an air flow meter provided in the internal combustion engine to measure an amount of the intake air flowing into the plurality of cylinders 11A, 11B, 11C and 11D. Further, when actually measuring concentration of the specific gas component in the internal combustion engine 1, the temperature of the exhaust gas G which are used when calculating the analysis data DS is actually measured. Parameters used for calculating the analysis data DS such as density, viscosity coefficient, specific heat and thermal conductivity can be determined based on data accumulated in the past, or may be actually measured instead.

As shown in FIG. 2, the catalyst converter 25 is disposed in the exhaust pipe 2, the catalyst converter 25 being capable of most efficiently purify HC (i.e., hydrocarbon) and CO (i.e., carbon monoxide). In the catalyst converter 25, the catalyst (there-way catalyst) 22 is disposed, in which noble metal particles are carried by a catalyst carrier. The catalyst carrier has a honeycomb structure having many vent holes, and the noble metal particles chemically reacts with toxic substances such as CO, HC, NOx and the like to convert them into relatively harmless substances. The catalyst carrier is composed of ceramic material, and the noble metal particles are composed of ceria-zirconia, Pt, Rh, Pd or the like.

In the simulation S, if the structure of the catalyst carrier having many vent holes is divided into each finite element by modeling, a lot of time is required. Hence, in the simulation S, whole catalyst 22 is replaced to a single resistor as a base having a predetermined size in which inertia coefficient and viscosity coefficient are set, thereby modeling the catalyst 22. The method of modelling is sometimes referred to as porous media method. Thus, simulation S can readily be performed. Further, the catalyst 22 in the actual equipment when acquiring actual measurement data DM can be fitted to the shape of the resistor of the catalyst 22 in the simulation S.

When acquiring the actual measurement data DM in the actual equipment, if noble metal particles are carried by catalyst 22 in the exhaust pipe 22, specific gas component in the exhaust gas G chemically react with others because of catalyst effect of the noble metal particle. In the case where the observation point X is positioned in downstream side of flow of the exhaust gas G with respect to the catalyst 22 in the exhaust pipe 2, this chemical reaction influences the concentration of the specific has component which is actually measured. Then, the analysis data DS is calculated assuming that no chemical reaction occurs on the catalyst 22 in the exhaust pipe 22. The actual measurement data DM is actually measured under a state where the catalyst 22 in the exhaust pipe 2 causes no chemical reaction.

Specifically, the catalyst 2 in the exhaust pipe 2 of the actual equipment may be, as a dummy catalyst, a catalyst carrier in which no noble metal particles are carried thereby. Note that y alumina or the like can be carried by the catalyst carrier so as to make a pressure loss in the dummy catalyst to be similar to a pressure loss in the actual catalyst. Assuming that no chemical reaction occurs on the catalyst 22, a change in concentration of the specific gas component in the exhaust gas G can be accurately measured over time, so that accuracy of evaluating the analysis data DS can be improved by the actual measurement data DM.

Also, temperature at which the noble metal particles in the catalyst 22 is capable of reacting with CO, HC, NOx or the like as catalytic action is a predetermined temperature or more, for example 300° C. or more. In this respect, the analysis data DS is obtained in a temperature range in which the catalyst 22 in the exhaust pipe 2 does not cause chemical reaction, and the actual measurement data DM can be measured in a temperature range in which the catalyst 22 in the exhaust pipe 2 does not cause chemical reaction. Also, in this case, accuracy of evaluating the analysis data using the actual measurement data can be improved.

In the case where the observation point C is located in the upstream side of the flow of the exhaust gas G than the position where the catalyst 22 in the converged pipe 23, chemical reaction occurring in the catalyst 22 rarely influences the actual measurement of the concentration of specific gas component at the observation point X. In this case, it is not necessary to obtain actual measurement data, by causing the catalyst 22 not to cause chemical reaction.

[Correlation]

As shown in FIG. 1, a correlation computer 5 performs determination whether difference between the analysis time interval TS and the actual time interval TM is within a predetermined correlated range, by comparing an average value of the analysis data DS calculated for a plurality of times and an equation of regression curve, with an average value of the actual measurement data DM calculated for a plurality of times, an equation of regression curve. The analysis data DS and the actual measurement data DM can be acquired for a plurality of times by changing any one of conditions among the virtual exhaust gas Gs and temperature of the exhaust gas G, an amount of flowing, a rotational speed of the internal combustion engine 1 (or inflow time interval T depending on the rotational speed of the internal combustion engine) or the like. The correlation computer 5 may be different from the analysis computer 3 and the measurement computer 4, or may be the same as the analysis computer 3 and the measurement computer 4.

The analysis data DS and the actual measurement data DM has positive correlation. When calculating the regression curve for the analysis data DS and the actual measurement data DM, the predetermined correlation range is determined such that the coefficient of determination $R^2$ is 0.8 or more where a correlation coefficient is R. In this case, when the analysis data DS and the actual measurement data DM are completely the same value, the coefficient of determination $R^2$ becomes 1. When comparing the average value of the analysis data DS and the average value of the actual measurement data DM, the predetermined correlation range can be defined such that a difference between the analysis data DS and the actual measurement data DM is within ±10%, for example.

The lengths of each input pipe portions 21A, 21B, 21C, 21D and the converged pipe portion 23, a cross-sectional area, a cross-sectional shape, entire shape of the exhaust pipe 2, influence the velocity distribution and the concentration distribution of the exhaust gas G in the converged pipe portion 23. The analysis time interval TS and the actual time interval TM are calculated or measured as a value offset from the inflow time interval T set in the analysis data DS or the actual measurement data DM, reflecting a change in the concentration of the virtual exhaust gas Gs or the concentration of the specific gas component G over time.

Accordingly, by checking/comparing between the analysis time interval TS and the actual measurement time interval TM, it can be confirmed whether or not parameters of the simulation S such as the flow velocity distribution and the concentration distribution of the virtual exhaust gas Gs in the converged pipe portion 23 is reflected to the same parameters of the actual measurement, i.e., the flow velocity distribution and the concentration distribution. Therefore, when the difference between the analysis time interval TS and the actual measurement time interval TM is within a predetermined correlation range, it is determined that the analysis data DS according to the simulation S correctly expresses the flow velocity distribution and the concentration distribution of the exhaust gas G in the converged pipe 23 with a predetermined accuracy.

(Effects and Advantages)

According to the analysis data DS, the identification information S4 is employed. Hence, the configuration can determine which cylinder exhausts the virtual exhaust gas Gs that reaches the observation point X of the converged pipe portion 23. On the other hand, in the actual measurement data DM, in order to determine a cylinder from which the exhaust gas G is exhausted and reached to the observation point X of the converged pipe portion 23, special method is required.

Accordingly, when calculating the actual measurement time interval TM in the actual measurement data DM, the air/fuel ratio of the specific cylinder and the air/fuel ratio of the rest of cylinders are set to be different from each other. The difference of the air/fuel ratios influences the concentration of specific gas components contained in the exhaust gas G, such as NOx (nitrogen oxides), CO (carbon monoxide), HC (hydrocarbon), oxygen or the like. According to the present embodiment, the air/fuel ratio of the specific cylinder is set to rich side and the air/fuel ratio of the rest of the cylinders are set to the theoretical air/fuel ratio, whereby the concentration of the exhaust gas G exhausted from the specific cylinder becomes significant higher than CO concentration of the exhaust gas G exhausted from the rest of the cylinders. Therefore, a change in the CO concentration of the exhausted gas G over time which is actually measured at the observation point X in the converged pipe 23 can be identified as a change in the CO concentration over time, which is contained in the exhausted gas G exhausted from the specific cylinder.

Thus, in the actual equipment of the internal combustion engine 1, substantially, actual time interval TM can be calculated based on the actual amplitude curve KM that represents a change in the concentration of the exhaust gas G over time, which is exhausted from the specific cylinder. Hence, the analysis time interval TS calculated for the specific cylinder and the actual time interval TM can be compared accurately.

The result of the simulation S based on the computational fluid dynamics analysis using the analysis computer 3 is appropriately evaluated by using the actual equipment. However, the evaluation method thereof has not been established. According to the evaluation method of the exhaust gas simulation of the present embodiment, a target of the simulation S is specific, that is, a gas flow of the exhaust gas G in the converged pipe portion 23 of the exhaust pipe 2 of the internal combustion engine. In this respect, by focusing on a fact that the internal combustion engine 1 has a plurality of cylinders 11A, 11B, 11C and 11D, and the exhaust gas G is sequentially exhausted to the cylinders 11A, 11B, 11C and 11D, a state of the exhaust gas G in any of the cylinders is set to be different from a state of the exhaust gas G in the rest of the cylinders, and a change in the concentration of the specific gas component is observed for the exhaust gas G exhausted from any of the cylinders. Thus, the result of simulation S can be simply and appropriately evaluated or verified by using the actual equipment.

The actual measurement data DM is acquired in the actual equipment of the internal combustion engine 1 by actually measuring a change in the concentration of a specific gas component in the exhaust gas G and not by measuring a change in the flow velocity of the exhaust gas G. In the case where the flow velocity of the exhaust gas G is actually measured, two detecting portions are required to be disposed in an upper stream side and a downstream side in the exhaust pipe 2, thereby measuring a time delay in a state change of the fluid between the pair of detecting portions. In this case, functions of radiating and detecting light are required for equipment of measuring the flow velocity so that the size of the equipment is likely to increase. Hence, it is difficult to dispose the equipment in such a complexed shaped portion in the exhaust pipe portion 2. When it is assumed that the flow velocity of the exhaust gas G is actually measured at a portion where turbulence, countercurrent or the like is being occurred in the vicinity of the input pipes 21A, 21B, 21C and 21D of the exhaust manifold, the accuracy thereof would be lowered.

On the other hand, according to the method for acquiring the actual measurement data DM described in the present embodiment, instead of using equipment for measuring the flow velocity, a gas analyzer 41 capable of measuring concentration of CO as a specific gas component. As the gas analyzer 41, for example, a fast response gas analyzer 41 HFR500 or the like which is manufactured by Cambustion Limited can be used. The shape of a measurement probe of the gas analyzer 411 is small so that this measurement probe 41 can be mounted to respective portions in the exhaust pipe 2. Further, since concentration of CO or the like is measured, the actual measurement can be accomplished, without lowering the measurement accuracy, even in the portions where turbulence, countercurrent or the like occurs. When acquiring the actual measurement data DM, a gas analyzer 41 having lower time resolution.

As described, according to the method for evaluating an exhaust gas simulation, validity of analysis data DS in accordance with the simulation S can be simply and appropriately evaluated.

Second Embodiment

Figure 8:
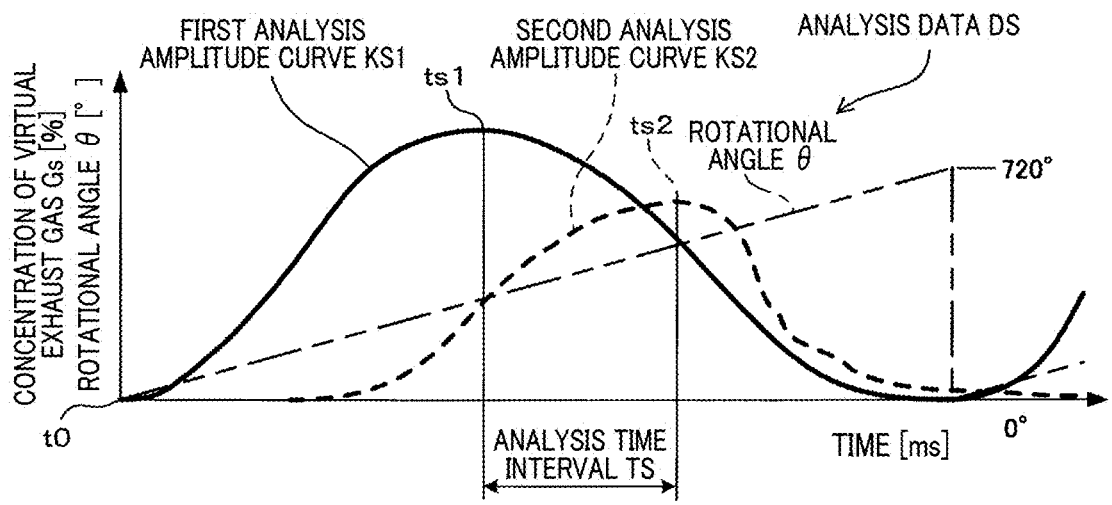
FIG. 8 is a graph showing a change in a virtual exhaust gas concentration and a rotational angle of a crank shaft in the analysis data according to a second embodiment.
Figure 9:
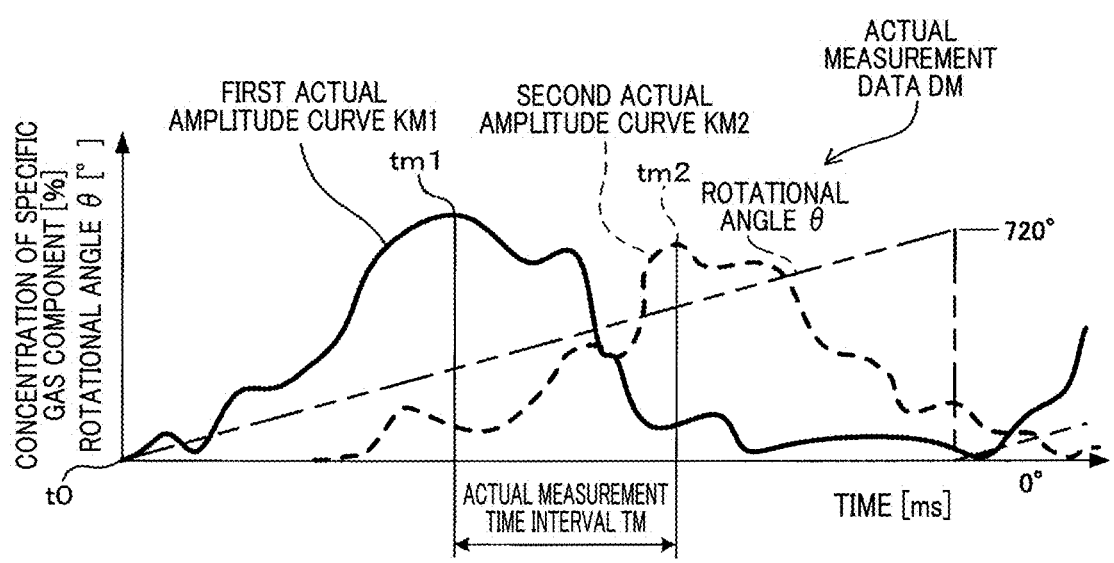
FIG. 9 is graph showing a change in a gas concentration of a specific gas in the exhaust gas and a rotational angle of the crank shaft in the actual measurement data according to the second embodiment.

In the method for evaluating an exhaust gas simulation according to the second embodiment, instead of acquiring the time intervals TS and TM for the analysis data DS and actual measurement data DM, which are defined as time intervals from the zero point t0 relative to the time course to the reference points is and tm of respective amplitude curves KS and KM, as shown in FIGS. 8 and 9, the analysis time intervals TS1 and TS2 (TS) between the reference points ts1 and ts2 of the analysis amplitude curves KS1 and KS2, and the actual time intervals TM1 and TM2 (TM) between the reference points tm1 and tm2 of the actual amplitude curve KM1 and KM2 are acquired.

When calculating the analysis data DS of the present embodiment, any two cylinders among the plurality of cylinders 11A, 11B, 11C and 11D of the internal combustion engine 1 are identified as a first specific cylinder and the second specific cylinder. An input pipe connected to the first specific cylinder is defined as a first specific input pipe and an input pipe connected to the second specific cylinder is defined as a second specific input pipe. The identification information S4 in the analysis data DS is set to distinguish the virtual exhaust gas Gs flowing into respective finite elements of the first specific input pipe from the first specific cylinder, the virtual exhaust gas Gs flowing into respective finite elements of the second specific input pipe from the second specific cylinder, the virtual exhaust gas Gs flowing into respective finite elements of the input pipes excluding the first and second specific input pipes from the cylinders excluding the first and second specific cylinders. The first specific cylinder and the first specific input pipe and the second specific cylinder and the second specific input pipe may be any of cylinder among the cylinders 11A, 11B, 11C and 11D and any of input pipe among the input pipes 21A, 21B, 21C and 21D.

As shown in FIG. 8, a change in concentration of a first virtual exhaust gas Gs is calculated as a first analysis amplitude curve KS1, where the concentration of the first virtual exhaust gas Gs represents a concentration that the virtual exhaust gas Gs exhausted to the exhaust pipe 2 from the first specific cylinder occupies the observation finite element YX at the observation point X of the converged pipe portion 23. Also, a change in concentration of a second virtual exhaust gas Gs is calculated as a second analysis amplitude curve KS2, where the concentration of the second virtual exhaust gas Gs represents a concentration that the virtual exhaust gas Gs exhausted to the exhaust pipe 2 from the second specific cylinder occupies the observation finite element YX at the observation point X of the converged pipe portion 23. Then, a time interval between the reference point ts1 in the first analysis amplitude curve KS1 and the reference point ts2 in the second analysis amplitude curve KS2 is calculated as the first analysis amplitude curve KS1. The reference points ts1 and ts2 may be set as the peak point, the bottom point and the center of the deviation or the like. Note that the analysis time interval TS may be an interference period in which the first analysis curve KS1 and the second amplitude analysis curve KS2 are interfered from each other.

According to the present embodiment, two cylinders at which subsequent combustion strokes are executed are defined as the first specific cylinder and the second specific cylinder. The first and second cylinders may be set as two cylinders at which combustion strokes are executed between combustion strokes executed by another cylinders.

On the other hand, as shown in FIG. 9, the actual measurement data DM is acquired such that concentration of the specific gas component at the observation point X in the converged pipe portion of the exhaust pipe 2 is actually measured for a case where the air/fuel ratio of the first specific cylinder and the air/fuel ratio of the rest of cylinders are set to be different from each other, and a case where the air/fuel ratio of the second specific cylinder and the air/fuel ratio of the rest of cylinders are set to be different from each other. First, in order to measure CO concentration as the specific gas component, the air/fuel ratio of the first specific cylinder is set to rich side and the air/fuel ratio of the rest of the cylinders excluding the first specific cylinder is set to the theoretical air/furl ratio, whereby a combustion operation of the internal combustion engine is performed. At this time, the gas analyzer 41 is used to actually measure the concentration of the specific gas component at the observation point X in the converged pipe portion 23 of the exhaust pipe 2. Since only the air/furl ratio of the first specific cylinder is set to rich side, the CO concentration of the exhaust gas G actually measured by the gas analyzer 41 can be identified as CO concentration of the exhaust gas G exhausted to the exhausted pipe 2 from the first specific cylinder. The concentration of the specific gas component is actually measured at predetermined sampling intervals, and a change in the concentration of the specific gas component is determined as the first actual amplitude curve KM1.

Next, the internal combustion engine 1 is operated as a combustion operation to actually measure the CO concentration as a specific gas component, under a condition in which the air/fuel ratio of the second specific cylinder is set to be on the rich side and the air/fuel ratio of the rest of the cylinders excluding the second specific cylinder is set to be the theoretical air/fuel ratio. At this time, the gas analyzer 41 actually measures concentration of the specific gas component at the observation point X of the converged pipe portion 23 in the exhaust pipe 2. Since only the air/fuel ratio of the second specific cylinder is set to be on the rich side, the concentration of the specific gas component in the exhaust gas G which is actually measured by the gas analyzer 41 can be identified as concentration of the specific gas component in the exhaust gas G exhausted to the exhaust pipe 2 from the second specific cylinder. Also, the concentration of the specific gas component is measured at predetermined sampling intervals, and a change in the concentration of the specific gas component is defined as a second actual amplitude curve KM2.

Subsequently, as shown in FIG. 9, a graph of the first actual amplitude curve KM1 and a graph of the second actual amplitude curve KM2 are combined when the zero points t0 between these graphs are aligned. In the combined graph, there is a time lag between concentration peak of the specific gas component in the first actual amplitude curve KM1 and concentration peak of the specific gas component in the second actual amplitude curve KM2. Then, the actual time interval TM is calculated as a time interval between the reference point tm1 in the first actual amplitude curve KM1 and the reference point tm2 in the second actual amplitude curve KM2. The reference points tm1 and tm2 can be set similar to a case of the analysis data DS. Note that the actual time interval TM can be also referred to as an interference period where the first actual amplitude curve KM1 and the second amplitude curve KM2 are interfered with each other.

Subsequently, similar to that of the first embodiment, the analysis data DS is determined as valid when the difference between the analysis time interval TS and the actual time interval TM is within a predetermined correlation range. According to the present embodiment, the analysis time interval TS calculated based on the concentration of the virtual exhaust gas GS of two cylinders and the actual time interval TM calculated based on the concentration of the specific gas components of two cylinders are compared, thereby evaluating validity of the analysis data DS. Hence, the flow velocity distribution and the concentration distribution of the exhaust gas G in the exhaust pipe 2 can be more reflected to the analysis data DS and the actual measurement data DM, so that accuracy of evaluating the validity of the analysis data DS can be improved.

In the method for evaluating an exhaust gas simulation according to the present embodiment, elements having the same reference numbers as the first embodiment and other embodiments are the same as that of the first embodiment, and similar operational effects of the first embodiment can be obtained.

Third Embodiment

Figure 10:
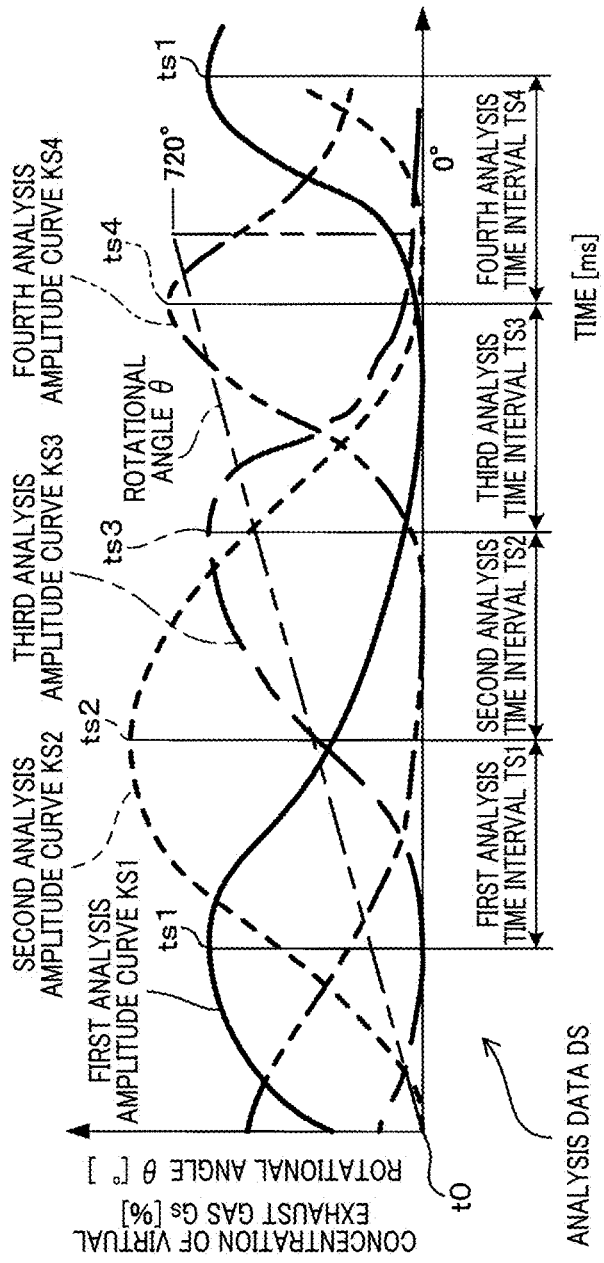
FIG. 10 is a graph showing a change in a virtual exhaust gas concentration and a rotational angle of a crank shaft in the analysis data according to a third embodiment.
Figure 11:
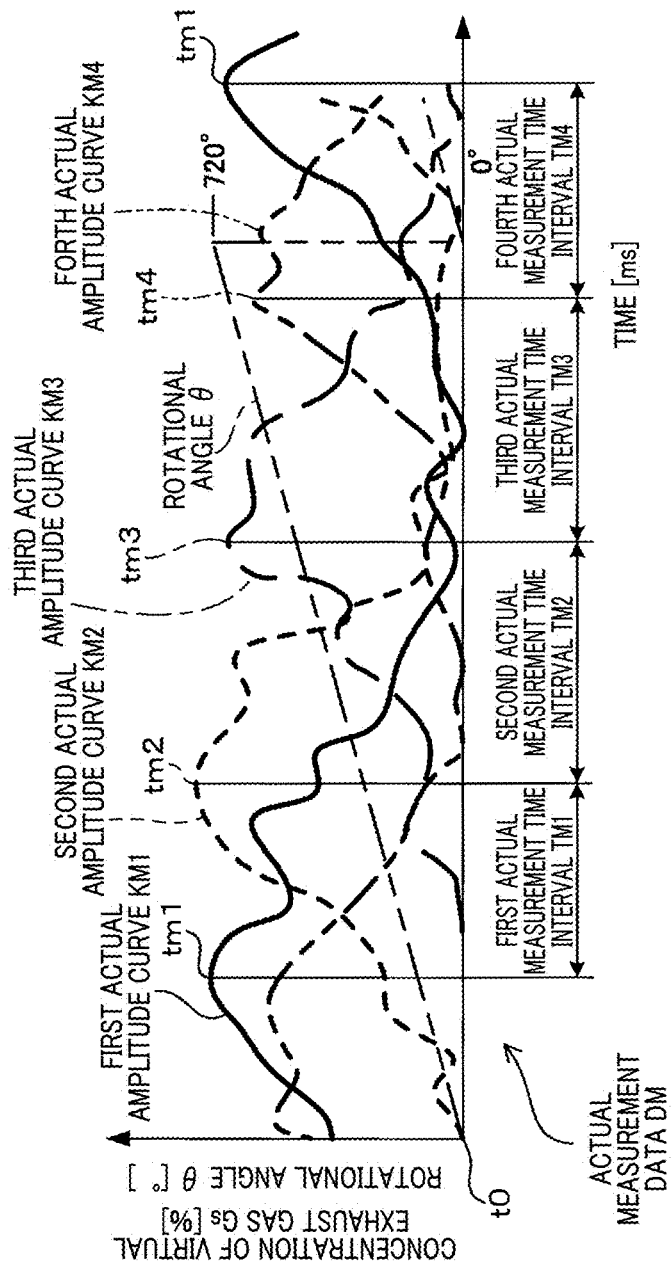
FIG. 11 is a graph showing a change in a gas concentration of a specific gas in the exhaust gas and a rotational angle of the crank shaft in the actual measurement data according to the third embodiment.

As shown in FIGS. 10 and 11, according to the method for evaluating an exhaust gas simulation of the third embodiment, the analysis time intervals TS1, TS2, TS3, TS4 between the reference points ts1, ts2, ts3 and ts4 of the analysis amplitude curve KS1, KS2, KS3, KS4, and the actual time intervals TM1, TM2, TM3 and TM4 between the reference point tm1, tm2, tm3 and tm4 of the actual amplitude curve KM1, KM2, KM3 and KM4 are calculated. According to the present embodiment, a case will be described in which the internal combustion engine has four cylinders. The four cylinders are defined as a first cylinder 11A, a second cylinder 11B, a third cylinder 11C and a fourth cylinder 11D, and input pipe portions connected to the respective cylinders are defined as a first input pipe portion 21A, a second input pipe portion 21B, a third input pipe portion 21C and a fourth input pipe portion 21D.

The identification information S4 in the analysis data DS of the present embodiment is set such that the virtual exhaust gasses entering respective finite elements Y of the four input pipe portions 21A, 21B, 21C and 21D from the four cylinders 11A, 11B, 11C and 11D are distinguished from each other. Specifically, the identification information S4 is set to mutually distinguish the virtual exhaust gas Gs entering respective finite elements Y of the first input pipe portion 21A from the first cylinder 11A, the virtual exhaust gas Gs entering respective finite elements Y of the second input pipe portion 21B from the second cylinder 11B, the virtual exhaust gas Gs entering respective finite elements Y of the third input pipe portion 21C from the third cylinder 11C, and the virtual exhaust gas Gs entering respective finite elements Y of the fourth input pipe portion 21D from the fourth cylinder 11D.

Also, as shown in FIG. 10, when obtaining the analysis data DS according to the present embodiment, a change in concentration of virtual exhaust gasses Gs observed at the observation finite element YX of the observation point X of the converged pipe portion 23 is calculated as the analysis amplitude curve KS1, KS2, KS3 and KS4 corresponding to respective cylinders 11A, 11B, 11C and 11D, where the virtual exhaust gasses Gs is exhausted to the exhaust pipe 2 from the respective cylinders 11A, 11B, 11C and 11D.

Specifically, the first cylinder 11A is defined as the specific cylinder, and a change in concentration of a first virtual exhaust gas Gs observed at the observation finite element YX is calculated as a first analysis amplitude curve KS1 corresponding to the cylinder 11A, in which the first virtual exhaust gas Gs is exhausted to the exhaust pipe 2 from the cylinder 11A. Also, the second cylinder 11B is defined as the specific cylinder, and a change in concentration of a second virtual exhaust gas Gs observed at the observation finite element YX is calculated as a second analysis amplitude curve KS2 corresponding to the cylinder 11B, in which the second virtual exhaust gas Gs is exhausted to the exhaust pipe 2 from the cylinder 11B. The third cylinder 11C is defined as the specific cylinder, and a change in concentration of a third virtual exhaust gas Gs observed at the observation finite element YX is calculated as a third analysis amplitude curve KS3 corresponding to the cylinder 11C, in which the third virtual exhaust gas Gs is exhausted to the exhaust pipe 2 from the cylinder 11C. Likewise, fourth cylinder 11D is defined as the specific cylinder, and a change in concentration of a fourth virtual exhaust gas Gs observed at the observation finite element YX is calculated as a fourth analysis amplitude curve KS3 corresponding to the cylinder 11D, in which the fourth virtual exhaust gas Gs is exhausted to the exhaust pipe 2 from the cylinder 11D.

Then, time intervals between mutually adjacent reference points ts1, ts2, ts3 and ts4 in the analysis amplitude curve KS1, KS2, KS3 and KS4 corresponding to the respective cylinders 11A, 11B, 11C and 11D are determined as the analysis time intervals TS1, TS2, TS3 and TS4. Specifically, a time interval between the reference point ts1 in the first analysis amplitude curve KS1 and the reference point ts2 in the second analysis amplitude curve KS2 is determined as a first analysis time interval TS1. Also, a time interval between the reference point ts2 in the second analysis amplitude curve KS2 and the reference point ts3 in the third analysis amplitude curve KS3 is determined as a second analysis time interval TS2. Further, a time interval between the reference point ts3 in the third analysis amplitude curve KS3 and the reference point ts4 in the fourth analysis amplitude curve KS4 is determined as a third analysis time interval TS3. Moreover, a time interval between the reference point ts4 in the fourth analysis amplitude curve KS4 and the reference point ts1 in the first analysis amplitude curve KS1 is determined as a fourth analysis time interval TS4. Each reference point ts1, ts2, ts3 and ts4 can be the peak point, the bottom point and the center of the deviation.

On the other hand, as shown in FIG. 11, when obtaining the actual measurement data DM according to the present embodiment, concentration of the specific gas component at the observation point X of the converged pipe portion 23 in the exhaust pipe 2 is actually measured for a case where the air/fuel ratio of the first cylinder 11A is set to be different that of rest of the cylinders, a case where the air/fuel ratio of the second cylinder 11B is set to be different that of rest of the cylinders, a case where the air/fuel ratio of the third cylinder 11C is set to be different that of rest of the cylinders, and a case where the air/fuel ratio of the fourth cylinder 11D is set to be different that of rest of the cylinders.

To measure actual CO concentration as the specific gas component, the air/fuel ratio of the first cylinder 11A is set as the specific cylinder and set the air/fuel ration thereof to be rich side, and the air/fuel ratio of rest of the cylinders are set to be the theoretical air/fuel ratio, and combustion operation of the internal combustion engine 1 is performed. At this time, the gas analyzer 41 is used to measure actual CO concentration at the observation point X of the converged pipe portion in the exhaust pipe 2. Since the air/fuel ratio is set to be rich side only for the first cylinder 11A, the concentration of the specific gas component actually measured by the gas analyzer 41 can be identified as concentration of a specific gas component in the exhaust gas G exhausted to the exhaust pipe 2 from the first cylinder 11A. Further, concentration of the specific gas component is measured at predetermined sampling intervals, and a change in the concentration of the specific gas component is determined as the first actual amplitude curve KM1.

As shown in FIG. 11, sequential specific cylinders are determined for second cylinder to fourth cylinders 11B, 11C and 11D, and a combustion operation of the internal combustion engine 1 is sequentially performed for the sequentially specific cylinders with the air/fuel ratio being set in rich side as similar to the first cylinder 11. At this time, for the second to fourth cylinders 11B, 11C and 11D, similar to the first cylinder 11A, a change in the concentration of the specific gas component is measured. Then, similar to the first actual amplitude curve KM1, the second actual amplitude curve KM2, the third actual amplitude curve KM3 and the fourth actual amplitude curve KM4 are calculated for the second cylinder 11B, the third cylinder 11C, and the fourth cylinder 11D respectively.

Next, a graph on which the first actual amplitude curve KM1 is shown, a graph on which the second actual amplitude curve KM2 is shown, a graph on which the third actual amplitude curve KM3 is shown, and a graph on which the fourth actual amplitude curve KM4 is shown are combined with the zero points t0 relative to the time course for each of the actual amplitude curves aligned. At this point, in the graph where four actual amplitude curves KM1, KM2, KM3 and KM4 are combined, a concentration peak of the specific gas component in the first actual amplitude curve KM1, a concentration peak of the specific gas component in the second actual amplitude curve KM2, a concentration peak of the specific gas component in the third actual amplitude curve KM3, and a concentration peak of the specific gas component in the fourth actual amplitude curve KM4, are displaced from each other relative to the time axis.

Then, as shown in FIG. 11, time intervals between mutually adjacent reference points tm1, tm2, tm3 and tm4 in the actual measurement amplitude curve KM1, KM2, KM3 and KM4 corresponding to the respective cylinders 11A, 11B, 11C and 11D are determined as the actual measurement time intervals TM1, TM2, TM3 and TM4. Specifically, a time interval between the reference point tm1 in the first actual amplitude curve KM1 and the reference point tm2 in the second actual amplitude curve KM2 is determined as a first actual time interval TM1. Also, a time interval between the reference point tm2 in the second actual amplitude curve KM2 and the reference point tm3 in the third actual amplitude curve KM3 is determined as a second actual time interval TM2. Further, a time interval between the reference point tm3 in the third actual amplitude curve KM3 and the reference point tm4 in the fourth actual amplitude curve KM4 is determined as a third actual time interval TM3. Moreover, a time interval between the reference point tm4 in the fourth actual amplitude curve KM4 and the reference point tm1 in the first actual amplitude curve KM1 is determined as a fourth actual time interval TM4. Each reference point tm1, tm2, tm3 and tm4 can be set similar to that of the analysis data DS.

Then, the process determines that the analysis data DS is valid, when the difference between the analysis time interval TS1 to TS4 and the actual time intervals TM1 to TM4 corresponding to the cylinders 11A to 11D is within a predetermined correlation range. According to the present embodiment, the process determines that analysis data DS is valid when a difference between the first analysis time interval TS1 and the first actual time interval TM1, a difference between the second analysis time interval TS2 and the second actual time interval TM2, a difference between the third analysis time interval TS3 and the third actual time interval TM3, and a difference between the fourth analysis time interval TS4 and the fourth actual time interval TM4 are within a predetermined correlation range.

According to the present embodiment, validity of the analysis data DS is evaluated by comparing the analysis time intervals TS1 to TS4 which are calculated based on the concentration of the virtual exhaust gas Gs in all cylinders, and the actual time intervals TM1 to TM4 calculated based on the concentration of the specific gas component of the all cylinders. Therefore, the flow velocity distribution and the concentration distribution of the exhaust gas G in the exhaust pipe 2 can be more reflected to the analysis data DS and the actual measurement data DM, so that accuracy of evaluating the validity of the analysis data DS can be improved.

In the method for evaluating an exhaust gas simulation according to the present embodiment, elements having the same reference numbers as the first embodiment and other embodiments are the same as that of the first embodiment, and similar operational effects of the first embodiment can be obtained.

<Confirmation Test>

Figure 12:
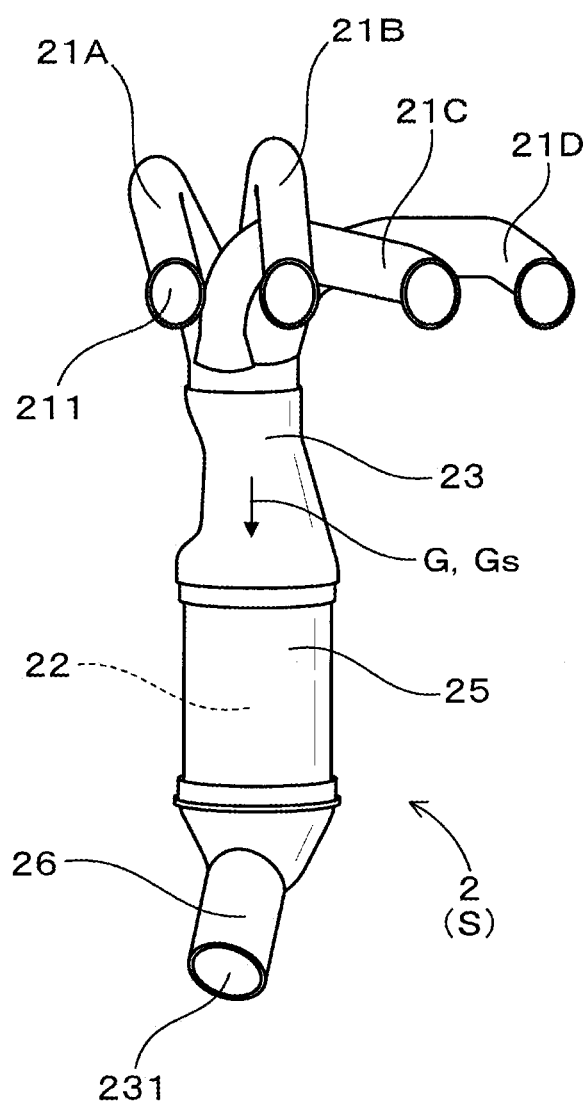
FIG. 12 is an explanatory diagram according to a confirmation test, showing an internal combustion engine and an exhaust pipe.

In the confirmation test, with the evaluation method of the exhaust simulation described in the third embodiment, the analysis data DS and the actual measurement data DM are obtained and the validity of the analysis data DS was evaluated. As shown in FIG. 12, in the internal combustion engine 1 and the exhaust pipe 2 of the confirmation test, cylinders and input pipe portions arranged sequentially from one end portion to the other end portions are defined as the first to fourth cylinders 11A, 11B, 11C and 11D, and the first to fourth input pipe portions 21A, 21B, 21C and 21D. For the first to fourth cylinders 11A, 11B, 11C and 11D, combustion strokes are performed in the order of the first cylinder 11A, the third cylinder 11C, the fourth cylinder 11D and the second cylinder 11B, and the exhaust gas G is exhausted from the cylinders in this order to the exhaust pipe 2.

For the software that performs the simulation S, Star-CCM+ produced by Siemens. For the actual equipment of the internal combustion engine 1, 2AR-FE (displacement: 2.493 litter) engine manufactured by Toyota Motor, which is an in-line four-cylinder reciprocating engine, was used. As the physical property value S1 of the virtual exhaust gas Gs in the analysis data DS, a density of 0.424 (kg/m$^3$), viscosity coefficient of $9.14 \times 10^{-5}$ (Pa/s), specific heat of 1.118 (J/gK), thermal conductivity of 0.0613 (W/mK), and temperature of 560° C. are used to conform to data of the actual equipment.

The flow velocity of the virtual exhaust gas Gs at the input 211 of the input pipe portions 21A, 21B, 21C and 21D is 4.625 (m/s) and the pressure of the virtual exhaust gas Gs in the output 231 of the converged pipe portion 23 is 1.725 (kPa). The inflow time interval T that represents the interval for performing the combustion strokes in the respective cylinders 11A, 11B, 11C, 11D is set to be 20 (ms). These values are the same as that of the actual equipment. "ms" represents $10^{-3}$ s, i.e., millisecond.

The catalyst 22 disposed in the exhaust pipe 2 is composed of a single resistor having a size of φ103 mm×105 mm, with 26.233 (kg/m$^4$) of inertia coefficient of the resistor, and 747.12 (kg·s/m$^3$) of viscosity coefficient of the resistor. Note that metal particles are not supported by the resistor.

Figure 13:
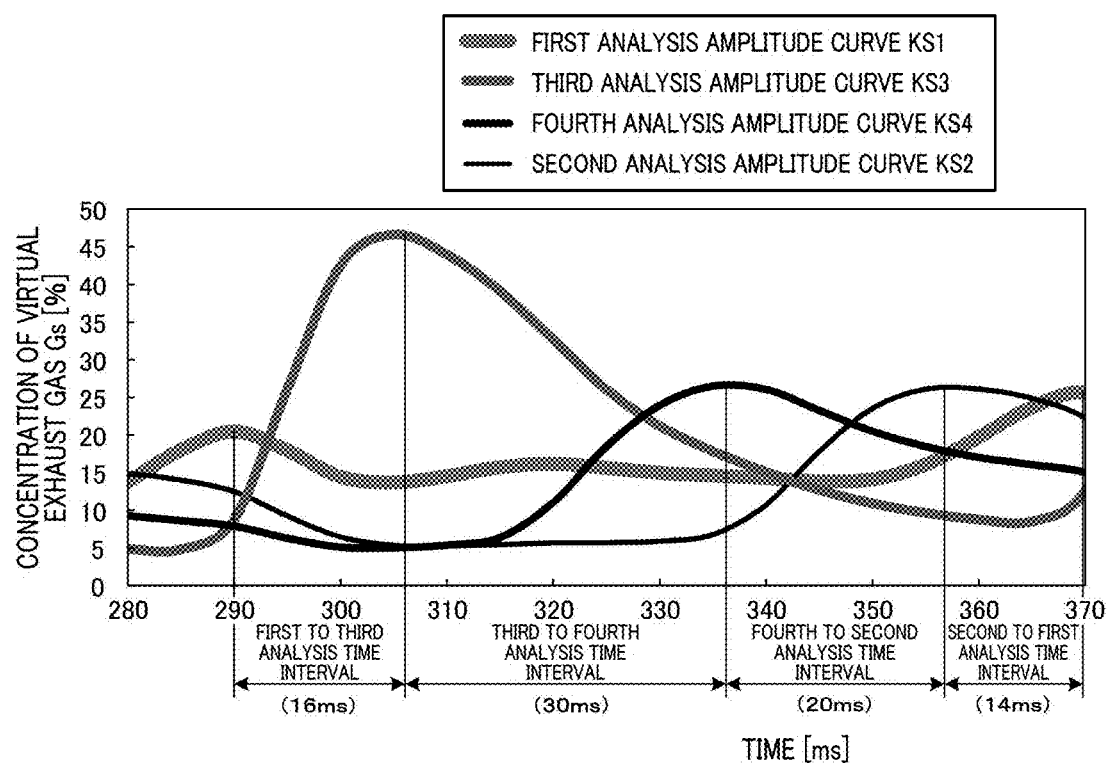
FIG. 13 is a graph according to the confirmation test, showing a change in a virtual exhaust gas concentration in the analysis data.

FIG. 13 shows analysis data DS obtained by performing the simulation S. In FIG. 13, the first to fourth analysis amplitude curves KS1, KS2, KS3 and KS4 are shown. In the present test, a case where the first cylinder 11A is determined as the specific cylinder corresponds to the first analysis amplitude curve KS1, a case where the third cylinder 11C is determined as the specific cylinder corresponds to the second analysis amplitude curve KS2, a case where the fourth cylinder 11D is determined as the specific cylinder corresponds to the fourth analysis amplitude curve KS4, and a case where the second cylinder 11B is determined as the specific cylinder corresponds to the second analysis amplitude curve KS2. Moreover, FIG. 13 shows a first-third analysis time interval between the peak point of the first analysis amplitude curve KS1 and the third analysis amplitude curve KS3, a third-fourth analysis time interval between the peak point of the third analysis amplitude curve KS3 and the fourth analysis amplitude curve KS4, a fourth-second analysis time interval between the peak point of the fourth analysis amplitude curve KS4 and the second analysis amplitude curve KS2, and a second-first analysis time interval between the peak point of the second analysis amplitude curve KS2 and the first analysis amplitude curve KS1.

Referring to FIG. 13, each time interval can be read such as the first-third analysis time interval TS3 is set to 16 ms, the third-fourth analysis time interval TS4 is set to 30 ms, the fourth-second analysis time interval TS2 is set to 20 ms, the second-first analysis time interval TS1 is set to 14 ms. Each of the time intervals between combustion strokes performed in the respective cylinders 11A, 11B, 11C and 11D is 20 ms. However, when the virtual exhaust gasses Gs exhausted from the cylinders 11A, 11B, 11C and 11D reach the observation point X of the exhaust pipe 2, respective analysis time intervals are offset from 20 ms.

Figure 14:
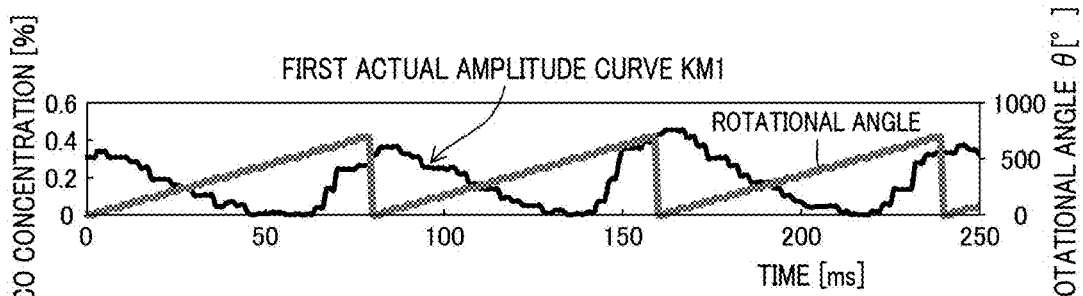
FIG. 14 is a graph according to the confirmation test, showing a change in CO concentration of the exhaust gas and a rotational angle of the crank shaft when the first cylinder is defined as a specific cylinder in the actual measurement data.
Figure 15:
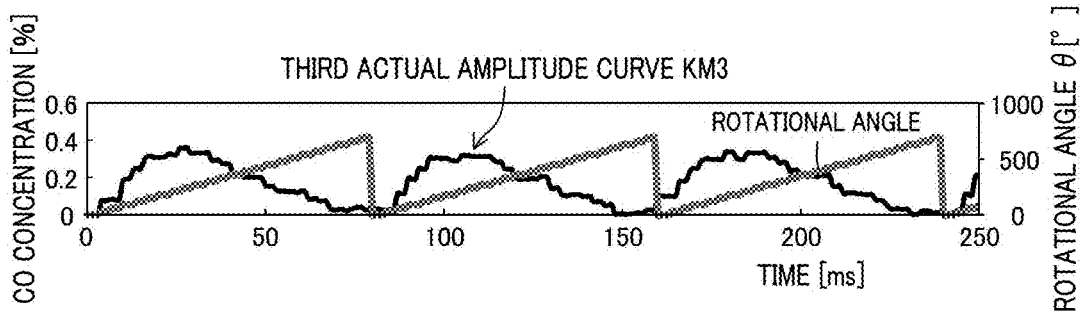
FIG. 15 is a graph according to the confirmation test, showing a change in CO concentration of the exhaust gas and a rotational angle of the crank shaft when the third cylinder is defined as a specific cylinder in the actual measurement data.
Figure 16:
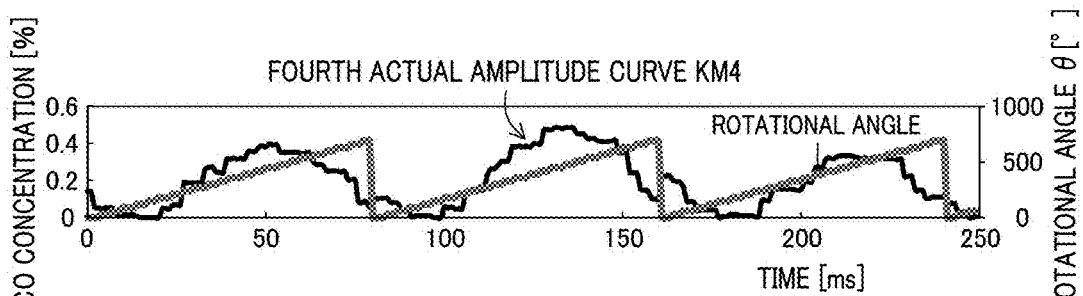
FIG. 16 is a graph according to the confirmation test, showing a change in CO concentration of the exhaust gas and a rotational angle of the crank shaft when the fourth cylinder is defined as a specific cylinder in the actual measurement data.
Figure 17:
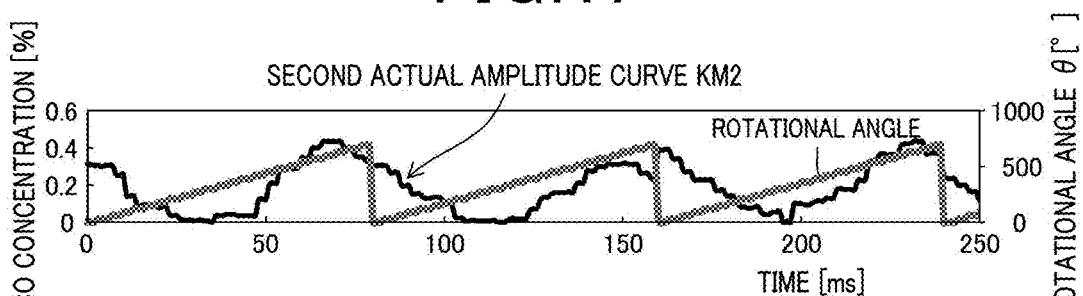
FIG. 17 is a graph according to the confirmation test, showing a change in CO concentration of the exhaust gas and a rotational angle of the crank shaft when the second cylinder is defined as a specific cylinder in the actual measurement data.

FIGS. 14 to 17 illustrates actual amplitude curves KM1, KM2, KM3 and KM4, which are a change in CO concentration actually measured in the actual internal combustion engine 1. FIG. 14 illustrates a first actual amplitude curve KM1 in which the air/fuel ratio is set to rich side only for the first cylinder 11A, FIG. 15 illustrates a third actual amplitude curve KM3 in which the air/fuel ratio is set to rich side only for the third cylinder 11C, FIG. 16 illustrates a fourth actual amplitude curve KM4 in which the air/fuel ratio is set to rich side only for the fourth cylinder 11D, and FIG. 17 illustrates a second actual amplitude curve KM2 in which the air/fuel ratio is set to rich side only for the second cylinder 11B. It should be noted that rest of cylinders in which the air/fuel ratio is set to be theoretical air/fuel ratio.

In FIGS. 14 to 17, rotational angle θ of the crank shaft 12 of the internal combustion engine 1 is also illustrated. The rotational angle θ repeatedly changes in a range from 0° to 720° depending on four strokes of the four-cycle engine.

Figure 18:
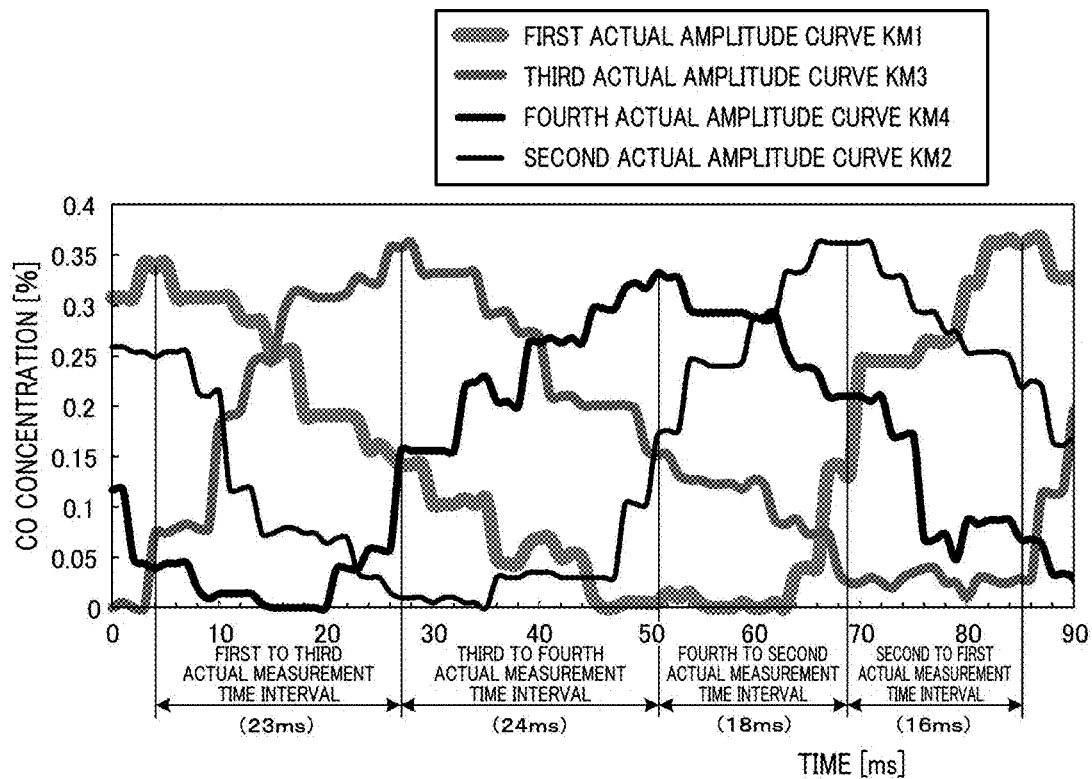
FIG. 18 is a graph according to the confirmation test, showing CO concentrations of the exhaust gas for respective cylinders in the actual measurement data.

FIG. 18 illustrates a graph in which the first to fourth actual amplitude curves KM1, KM2, KM3 and KM4 are combined under a condition where time points of 0° rotational angle θ of the crank shaft 12 are aligned between respective curves KM1, KM2, KM3 and KM4, which corresponds to zero points t0 relative to the time course. In FIG. 18, a first-third actual time interval between a peak point of the first actual amplitude curve KM1 and a peak point of the third actual amplitude KM3, a third-fourth actual time interval between a peak point of the third actual amplitude curve KM3 and a peak point of the fourth actual amplitude curve KM4, a fourth-second actual time interval between a peak point of the fourth actual amplitude curve KM4 and a peak point of the second actual amplitude KM2, and a second-first actual time interval between a peak point of the second actual amplitude curve KM2 and a peak point of the first actual amplitude KM1, are illustrated.

With reference to FIG. 18, the first to third actual time interval is 23 msec, the third-fourth time interval is 24 msec, the fourth-second actual time intervals is 18 msec, and the second-first actual time interval is 16 msec. The time interval between the cylinders 11A, 11B, 11C and 11D is 20 msec. However, when the exhaust gas G exhausted from the cylinders 11A, 11B, 11C and 11D reach the observation point X of the exhaust pipe 2, each actual time interval is offset from 20 msec depending on shapes, lengths or the like.

According to the present confirmation test, an amount of flow of the virtual exhaust gas Gs flowing into respective input pipe portions 21A, 21B, 21C and 21D and the rotational speed of the crank shaft 12 of the internal combustion engine 1 are appropriately changed, and each of the analysis time intervals of data DS and the actual measurement time intervals of the actual measurement data are obtained for plurality of times. The result of the test is shown in table 1 as follows.

TABLE 1

| | Analysis (Measurement) time interval | Analysis data | Measurement data |
|---|---|---|---|
| First data | 1st to 3rd | 16 | 23 |
| | 3rd to 4th | 30 | 24 |
| | 4th to 2nd | 20 | 18 |
| | 2nd to 1st | 16 | 16 |
| Second data | 1st to 3rd | 16 | 18 |
| | 3rd to 4th | 24 | 22 |
| | 4th to 2nd | 18 | 18 |
| | 2nd to 1st | 24 | 24 |
| Third data | 1st to 3rd | 7 | 8 |
| | 3rd to 4th | 10 | 8 |
| | 4th to 2nd | 10 | 10 |
| | 2nd to 1st | 9 | 10 |
| Fourth data | 1st to 3rd | 6 | 8 |
| | 3rd to 4th | 9 | 8 |
| | 4th to 2nd | 11 | 12 |
| | 2nd to 1st | 11 | 10 |

In the table 1, the first data shows a result of the case where an amount of flow corresponding to the virtual exhaust gas Gs and the exhaust gas G at the input 211 of the input pipe portions 21A, 21B, 21C and 21D is 10 g/sec, and the rotational speed is 1500 r.p.m. The second data shows a result of the case where the amount of flow is 25 g/sec, and the rotational speed is 1500 r.p.m. The third data shows a result of the case where the amount of flow is 40 g/sec and the rotational speed is 3000 r.p.m. The fourth data shows a result of the case where the amount of flow is 25 g/sec and the rotational speed is 3000 r.p.m.

Figure 19:
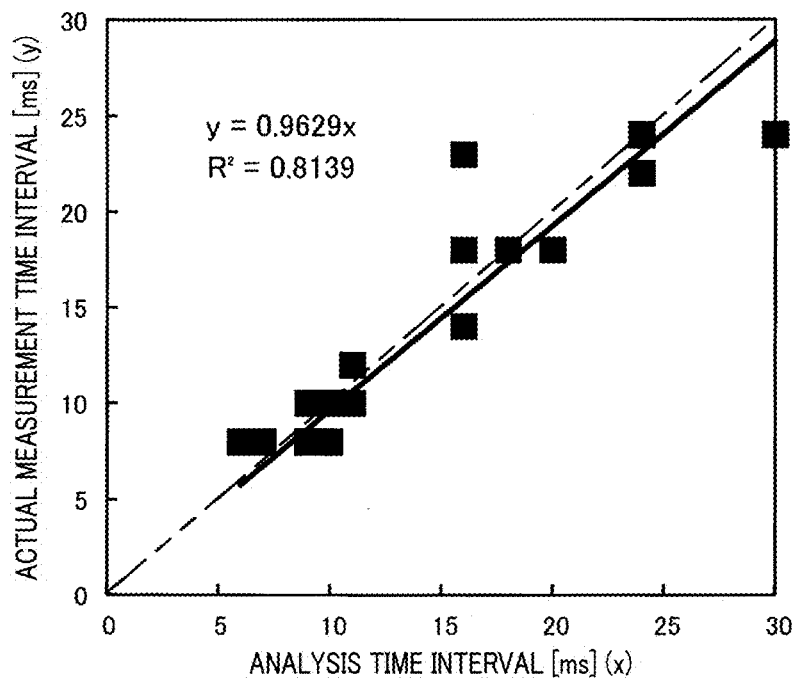
FIG. 19 is a graph according to the confirmation test, showing a relationship between respective analytical time intervals and respective actual measurement time intervals in the analysis data.

FIG. 19 illustrates a relationship between the analysis time intervals of the analysis data DS and the actual measurement data DM and the actual measurement time intervals of the actual measurement data DM. In FIG. 19, the analysis time intervals of the analysis data DS is expressed as x, the actual measurement time intervals of the measurement data DM is expressed as y, and a case is shown in which a line L1 defined as y=x completely coincides with the analysis data DS and the actual measurement data DM. As a result of a linear regression analysis for a relationship between the analysis time intervals and the actual measurement time intervals, a relationship equation y=9629x is obtained.

At this time, as a degree of a correlation between the analysis time intervals and the actual measurement time intervals, a decision coefficient $R^2$ with a correlation coefficient R is acquired. The result was $R^2$=0.8139, and it was confirmed that the decision coefficient $R^2$ was 0.8 or more. Accordingly, validity of the analysis data DS of the simulation S with this test was confirmed.

Other Embodiment

The actual amplitude curve KM in the actual measurement data DM can be modified by smoothing the curve thereof with various methods, thereby allowing the reference points of the actual amplitude curve KM to be readily readable. For example, the actual amplitude curve KM in the actual measurement data DM may be formed such that a change in the concentration of the specific gas component is averaged for a plurality of periods, as a single period data.

Figure 20:
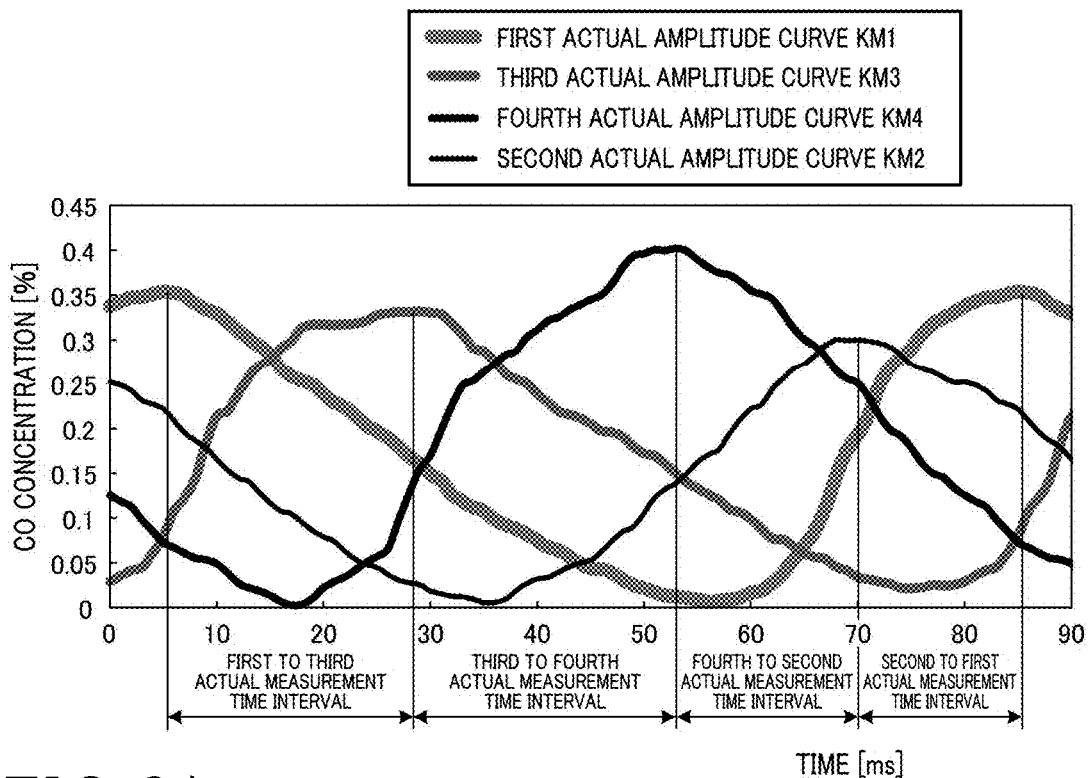
FIG. 20 is a graph according to other embodiment, showing a change in respective averaged CO concentrations of the exhaust gas in the first data of the actual measurement data.
Figure 21:
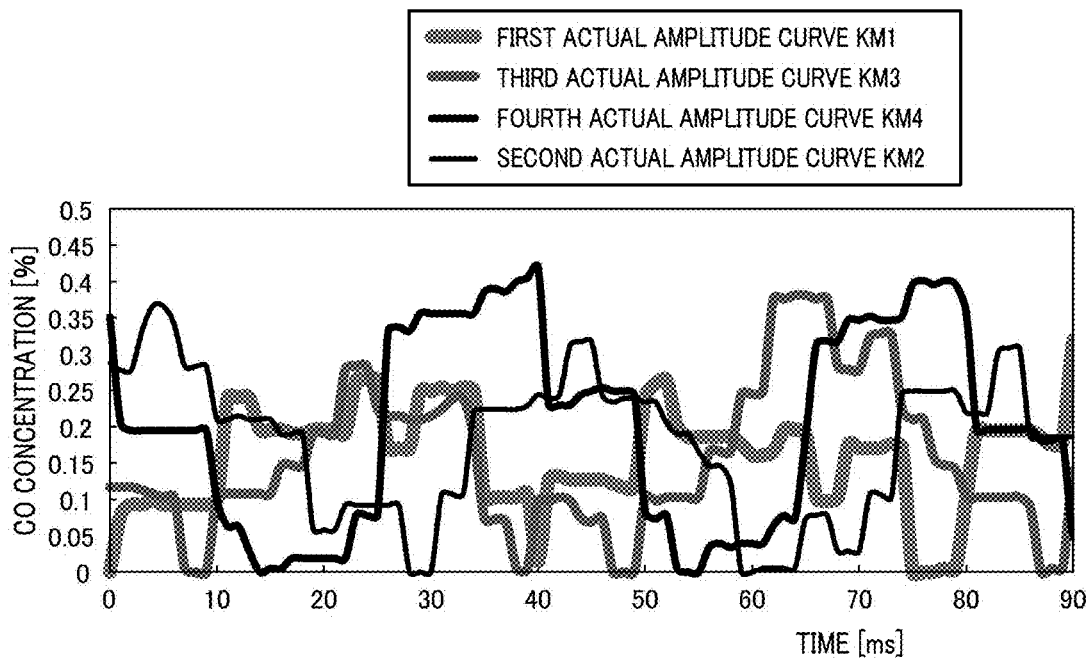
FIG. 21 is a graph according to other embodiment, showing a change in respective pre-averaged CO concentrations of the exhaust gas in the third data of the actual measurement data.
Figure 22:
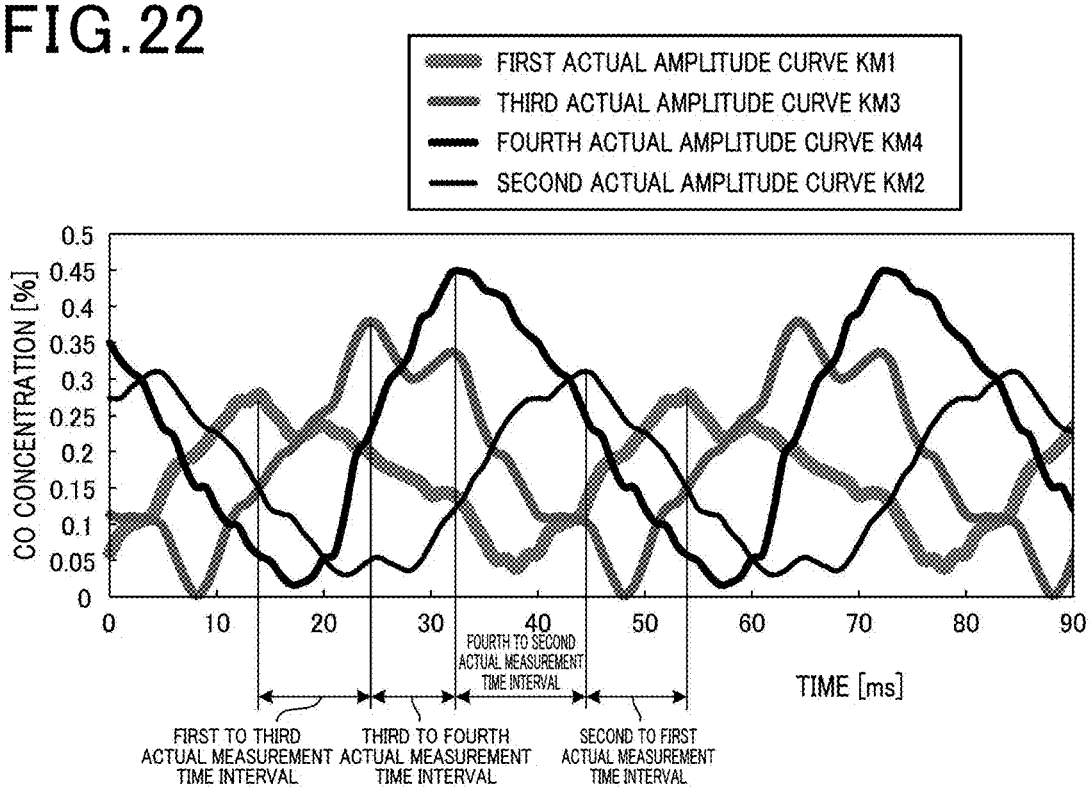
FIG. 22 is a graph according to other embodiment, showing a change in respective averaged CO concentrations of the exhaust gas in the third data of the actual measurement data.

FIG. 20 illustrates a graph in which actual amplitude curves KM1, KM2, KM3 and KM4 of the first data in the confirmation test was averaged. FIG. 21 illustrates a graph in which actual amplitude curves KM1, KM2, KM3 and KM4 of the third data in the confirmation test was not yet averaged. FIG. 22 illustrates a graph in which actual amplitude curves KM1, KM2, KM3 and KM4 of the third data in the confirmation test was averaged. FIGS. 20 and 22 illustrates average values for each of the first to fourth actual amplitude curves KM1, KM2, KM3 and KM4 when a combustion stroke of the internal combustion engine 1 is repeatedly performed for 50 times. In this case, respective actual amplitude curves KM1, KM2, KM3 and KM4 are smoothed so that the reference points and actual measurement time intervals in the actual amplitude curves KM1, KM2, KM3 and KM4 can readily be calculated.

Specifically, in the third data before performing the averaging process for the curves shown in FIG. 21, each waveform of the actual amplitude curves KM1, KM2, KM3 and KM4 is distorted so that reference points such as peak points are difficult to determine. In this case, as shown in FIG. 22, waveforms corresponding to actual amplitude curves KM1, KM2, KM3 and KM4 can be shaped by the averaging process, so that the reference points such as peak points or the like can readily be determined.

In the case where the reference points of the actual amplitude curves KM are set as peak points or bottom points, the peak points or the bottom points of the actual amplitude curves KM can be determined as points where gradient per unit of time of the actual amplitude curve KM become 0. This gradient indicates an amount of change in concentration of the specific gas component per unit of time. When obtaining the gradient, for respective actual amplitude curves KM, a difference between the concentration of the specific gas component obtained at previous sampling time, and the concentration of the specific gas component obtained at current sampling time is calculated for concentration of the specific gas component actually measured at predetermined sampling intervals. Then this difference is determined as a gradient of the actual amplitude curve KM per unit of time.

Figure 23:
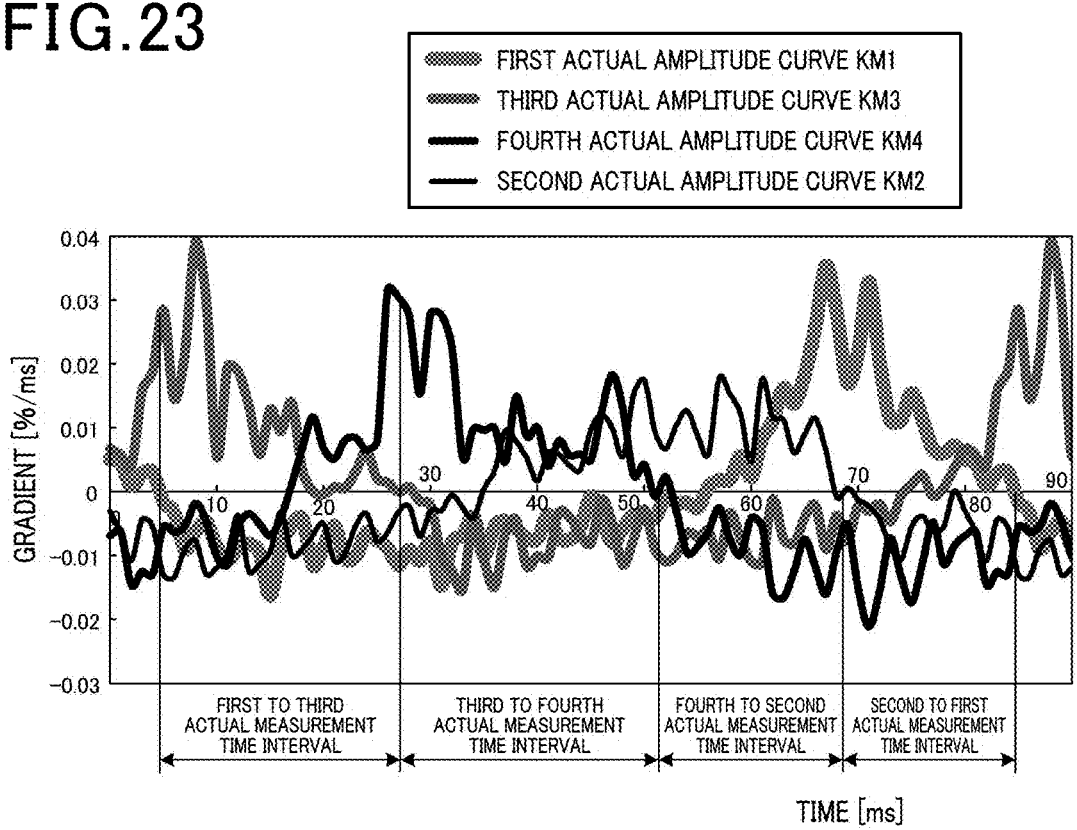
FIG. 23 is a graph according to other embodiment, showing respective slopes per time of a change in the CO concentrations of the exhaust gas in the first data of the actual measurement data.

FIG. 23 is a graph illustrating calculation result of the gradient per unit of time for the first to fourth actual amplitude curves KM1, KM2, KM3 and KM4 for the first data in the confirmation test. Note that the first to fourth actual amplitude curves KM1, KM2, KM3 and KM4 used for calculating the gradient correspond to the first data in which an averaging process shown in FIG. 20 was performed. When using this gradient, the reference points and actual time intervals for the actual amplitude curves KM1, KM2, KM3 and KM4 can more readily be calculated.

In peak points and bottom points in the first to fourth actual amplitude curves KM1, KM2, KM3 and KM4, an amount of change per unit of time of the concentration of the specific gas component becomes minimum and the gradient value becomes zero as well. However, due to variation during the actual measurement, the gradient value may become zero at points which are not peak points nor bottom points. The peak points or the bottom point may be determined based on not only a graph showing gradient per unit of time, but both of a graph showing gradient and a graph of the actual amplitude curve KM with or without averaging process being performed.

Although illustration is omitted, in the case where the reference points of the analysis amplitude curve KS are set as peak points or bottom points, the peak points or the bottom points of the analysis amplitude curve KS may be calculated as points at which the gradient per unit of time becomes zero. In this case, the peak point or the bottom points in the analysis amplitude curve KS can readily be calculated.

The present disclosure is not limited to the above-described embodiments, various modifications can be made without departing from the scope of spirit of the present disclosure.

What is claimed is:

1. A method for evaluating an exhaust gas simulation, wherein
a computer simulation based on a fluid dynamics analysis and an actual measurement are applied to an exhaust gas flow which is a flow of an exhaust gas in an exhaust pipe of an internal combustion engine so as to obtain an analysis data and a measurement data respectively, the exhaust pipe having a converged pipe portion in which a plurality of input pipe portions are converged and a catalyst is disposed, the input pipe portions being respectively connected to a plurality of cylinders of the internal combustion engine;
the computer simulation and the actual measurement are applied to the exhaust gas flow in the converged pipe portion, and the analysis data and the measurement data are compared, thereby evaluating a validity of the analysis data,
the method comprising steps of:
setting, in the analysis data, various conditions including a three-dimensional shaped model of the exhaust pipe, a physical property of a virtual exhaust gas, an inflow time interval of the virtual exhaust gas between the plurality of cylinders in which the virtual exhaust gas successively flows into the input pipe portions at a constant time interval, an inflow boundary condition of the virtual exhaust gas at an input of the input pipes, and an outflow boundary condition of the virtual exhaust gas at an output of the converged pipe portion;
determining any of cylinders in the plurality of cylinders to be a specific cylinder and the input pipe portion connected to the specific cylinder to be a specific input portion;
dividing the area of the exhaust pipe into a plurality of finite elements;
setting, when calculating transfer of the virtual exhaust gas between the finite elements, identification information to identify a virtual exhaust gas flowing into the finite elements of the specific input pipe portion from the specific cylinder, and a virtual exhaust gas flowing into the finite elements of the rest of input pipe portions excluding the specific input pipe portion from the rest of the cylinders excluding the specific cylinder;
calculating an analysis amplitude curve representing a change in concentration of the virtual exhaust gas with time at an observation finite element in the observation point of the converged pipe portion, the virtual exhaust gas being exhausted from the specific cylinder to the exhaust pipe, and an analysis time interval representing a time interval from a zero point relative to the time course during the computer simulation to the reference point in the analysis amplitude curve;
setting, in the measurement data, an air-fuel ratio of the rest of the cylinders excluding the specific cylinder to be within a predetermined range and an air-fuel ratio of the specific cylinder to be beyond the predetermined range;
measuring, for the exhaust gas exhausted to the exhaust pipe from the specific cylinder during a combustion operation of the internal combustion engine, a change in the specific gas component with time at the observation point of the converged pipe portion, thereby obtaining an actual amplitude curve;
calculating a time interval from a zero point in the measuring to a reference point in the actual amplitude curve to obtain an actual time interval; and
determining that the analysis data is valid, when a difference between the analysis time interval and the actual time interval is within a predetermined correlation range.

2. A method for evaluating an exhaust gas simulation, wherein
a computer simulation based on a fluid dynamics analysis and an actual measurement are applied to an exhaust gas flow which is a flow of an exhaust gas in an exhaust pipe of an internal combustion engine so as to obtain an analysis data and a measurement data respectively, the exhaust pipe having a converged pipe portion in which a plurality of input pipe portions are converged and a catalyst is disposed, the input pipe portions being respectively connected to a plurality of cylinders of the internal combustion engine;
the computer simulation and the actual measurement are applied to the exhaust gas in the converged pipe portion, and the analysis data and the measurement data are compared, thereby evaluating a validity of the analysis data,
the method comprising steps of:
setting, in the analysis data, various conditions including a three-dimensional shaped model of the exhaust pipe, a physical property of a virtual exhaust gas, an inflow time interval of the virtual exhaust gas between the plurality of cylinders in which the virtual exhaust gas successively flows into the input pipe portions at a constant time interval, an inflow boundary condition of the virtual exhaust gas at an input of the input pipes, and an outflow boundary condition of the virtual exhaust gas at an output of the converged pipe portion;
determining any of two cylinders in the plurality of cylinders to be a first specific cylinder and a second specific cylinder, the input pipe portion connected to the first specific cylinder to be a first specific input portion and the input pipe portion connected to the second specific cylinder to be a second specific input portion;
dividing the area of the exhaust pipe into a plurality of finite elements;
setting, when calculating transfer of the virtual exhaust gas between the finite elements, identification information to mutually identify a virtual exhaust gas flowing into the finite elements of the first specific input pipe portion from the first specific cylinder, a virtual exhaust gas flowing into the finite elements of the second specific input pipe portion from the second specific cylinder, a virtual exhaust gas flowing into the finite elements of the rest of input pipe portions excluding the first and second specific input pipe portions from the rest of the cylinders excluding the first and second specific cylinders;

calculating a first analysis amplitude curve representing a change in concentration of a first virtual exhaust gas with time at an observation finite element in the observation point of the converged pipe portion, the first virtual exhaust gas being exhausted from the first specific cylinder to the exhaust pipe, a second analysis amplitude curve representing a change in concentration of a second virtual exhaust gas with time at an observation finite element in the observation point of the converged pipe portion, the second virtual exhaust gas being exhausted from the second specific cylinder to the exhaust pipe, and an analysis time interval representing a time interval from a reference point in the first analysis amplitude curve to a reference point in the second analysis amplitude curve;

setting, when obtaining the measurement data, an air-fuel ratio of the rest of the cylinders excluding the first specific cylinder to be within a predetermined range and an air-fuel ratio of the first specific cylinder to be beyond the predetermined range;

measuring, for the exhaust gas exhausted to the exhaust pipe from the first specific cylinder during a combustion operation of the internal combustion engine, a change in the specific gas component with time at the observation point of the converged pipe portion, thereby obtaining a first actual amplitude curve;

setting, when obtaining the measurement data, an air-fuel ratio of the rest of the cylinders excluding the second specific cylinder to be within a predetermined range and an air-fuel ratio of the second specific cylinder to be beyond the predetermined range;

measuring, for the exhaust gas exhausted to the exhaust pipe from the second specific cylinder during a combustion operation of the internal combustion engine, a change in the specific gas component with time at the observation point of the converged pipe portion, thereby obtaining a second actual amplitude curve;

combining the first actual amplitude curve and the second actual amplitude curve when zero points between the first and second amplitude curves are aligned, and obtaining, as an actual time interval, a time interval from a reference point of the first actual amplitude curve to a reference point of the second actual amplitude curve; and determining that the analysis data is valid, when a difference between the analysis time interval and the actual time interval is within a predetermined correlation range.

3. A method for evaluating an exhaust gas simulation, wherein a computer simulation based on a fluid dynamics analysis and an actual measurement are applied to an exhaust gas flow which is a flow of an exhaust gas in an exhaust pipe of an internal combustion engine so as to obtain an analysis data and a measurement data respectively, the exhaust pipe having a converged pipe portion in which a plurality of input pipe portions are converged and a catalyst is disposed, the input pipe portions being respectively connected to a plurality of cylinders of the internal combustion engine;

the computer simulation and the actual measurement are applied to the exhaust gas in the converged pipe portion, and the analysis data and the measurement data are compared, thereby evaluating a validity of the analysis data, the method comprising steps of:

setting, in the analysis data, various conditions including a three-dimensional shaped model of the exhaust pipe, a physical property of a virtual exhaust gas, an inflow time interval of the virtual exhaust gas between the plurality of cylinders in which the virtual exhaust gas successively flows into the input pipe portions at a constant time interval, an inflow boundary condition of the virtual exhaust gas at an input of the input pipes, and an outflow boundary condition of the virtual exhaust gas at an output of the converged pipe portion;

determining any of cylinders in the plurality of cylinders to be a specific cylinder and the input pipe portion connected to the specific cylinder to be a specific input portion;

dividing the area of the exhaust pipe into a plurality of finite elements;

setting, when calculating transfer of the virtual exhaust gas between the finite elements, identification information to mutually identify each of virtual exhaust gasses flowing into respective finite elements corresponding to a plurality of input pipe portions from respective cylinders;

calculating, for the respective cylinders, analysis amplitude curves representing a change in concentration of the virtual exhaust gasses with time at an observation finite element in the observation point of the converged pipe portion, the virtual exhaust gasses being exhausted from the respective cylinders to the exhaust pipe, and analysis time intervals representing time intervals between mutually adjacent reference points in the analysis amplitude curves for respective cylinders;

setting, in the measurement data, an air-fuel ratio of the rest of the cylinders excluding a specific cylinder selected from the plurality of cylinders to be within a predetermined range and an air-fuel ratio of the specific cylinder to be beyond the predetermined range;

measuring, for the exhaust gas exhausted to the exhaust pipe from the specific cylinder during a combustion operation of the internal combustion engine, a change in the specific gas component with time at the observation point of the converged pipe portion, and determining the change in the specific gas component as actual amplitude curves;

measuring the actual amplitude curves for respective cylinders under a condition that each of the cylinders is sequentially set as the specific cylinder;

combining the measured actual amplitude curves when zero points between the measured actual amplitude curves are aligned, and obtaining, as actual time intervals for respective cylinders, time intervals between mutually adjacent reference points in the measured actual amplitude curves for respective cylinders; and determining that the analysis data is valid, when a difference between the analysis time interval and the actual time interval for respective cylinders is within a predetermined correlation range.

4. The method for evaluating an exhaust gas simulation according to claim 1, wherein the fluid dynamics analysis includes an analysis for an exhaust gas flow based on finite volume method.

5. The method for evaluating an exhaust gas simulation according to claim 1, wherein
   the analysis data is obtained in a temperature range in which a catalyst in the exhaust pipe does not cause chemical reaction, or the analysis data is obtained assuming that the catalyst in the exhaust pipe does not perform chemical reaction; and
   the measurement data is measured in a temperature range in which the catalyst in the exhaust pipe does not cause chemical reaction, measured under a state where the catalyst in the exhaust pipe does not cause chemical reaction, or measured under a state where the observation point is disposed in an upstream side of an exhaust gas flow compared to a position of the catalyst in the converged pipe portion.

6. The method for evaluating an exhaust gas simulation according to claim 1, wherein
   the actual amplitude curve is formed such that a change in the concentration of the specific gas component is averaged for a plurality of periods, as a single period data.

7. The method for evaluating an exhaust gas simulation according to claim 2, wherein
   the reference point of the first actual amplitude curve to the reference point of the second actual amplitude curve are set as peak points or bottom points; and
   the peak points or the bottom points of the actual amplitude curves are determined as points where gradient per unit of time of the actual amplitude curve become 0.

\* \* \* \* \*